(12) United States Patent
Hayashi et al.

(10) Patent No.: US 12,064,438 B2
(45) Date of Patent: Aug. 20, 2024

(54) PHARMACEUTICAL PREPARATION EXCELLENT IN LIGHT STABILITY AND DISSOLUTION PROPERTY

(71) Applicant: Shionogi & Co., Ltd., Osaka (JP)

(72) Inventors: Naomi Hayashi, Hyogo (JP); Masato Gomi, Hyogo (JP); Shohei Aikawa, Hyogo (JP)

(73) Assignee: SHIONOGI & CO., LTD., Osaka (JP)

( * ) Notice: Subject to any disclaimer, the term of this patent is extended or adjusted under 35 U.S.C. 154(b) by 328 days.

(21) Appl. No.: 16/764,067

(22) PCT Filed: Nov. 15, 2018

(86) PCT No.: PCT/JP2018/042220
§ 371 (c)(1),
(2) Date: May 14, 2020

(87) PCT Pub. No.: WO2019/098259
PCT Pub. Date: May 23, 2019

(65) Prior Publication Data
US 2020/0375998 A1    Dec. 3, 2020

(30) Foreign Application Priority Data

Nov. 17, 2017  (JP) ................................ 2017-222068

(51) Int. Cl.
*A61K 31/5383*    (2006.01)
*A61K 9/20*    (2006.01)
*A61K 9/28*    (2006.01)
*A61P 31/16*    (2006.01)

(52) U.S. Cl.
CPC ........ *A61K 31/5383* (2013.01); *A61K 9/2054* (2013.01); *A61K 9/2813* (2013.01); *A61K 9/2846* (2013.01); *A61K 9/2866* (2013.01); *A61P 31/16* (2018.01)

(58) Field of Classification Search
CPC .......................... A61K 31/5358; A61P 31/16
See application file for complete search history.

(56) References Cited

U.S. PATENT DOCUMENTS

| | | | |
|---|---|---|---|
| 6,458,389 B1 | 10/2002 | Debregeas et al. | |
| 10,392,406 B2* | 8/2019 | Kawai | A61K 31/542 |
| 2005/0038072 A1* | 2/2005 | Yamaoka | C07D 405/06 |
| | | | 546/208 |
| 2008/0014321 A1 | 1/2008 | Schweinfurth et al. | |
| 2009/0215700 A1* | 8/2009 | Asami | A61P 31/00 |
| | | | 514/1.3 |
| 2011/0009347 A1* | 1/2011 | Liang | A61P 43/00 |
| | | | 514/23 |
| 2012/0009259 A1* | 1/2012 | Delaet | A61K 9/2013 |
| | | | 514/444 |
| 2014/0242158 A1* | 8/2014 | Nishiura | A61K 9/1635 |
| | | | 424/490 |
| 2014/0287034 A1* | 9/2014 | Fretzen | A61K 38/12 |
| | | | 424/452 |
| 2015/0140036 A1* | 5/2015 | Mannick | A61P 3/10 |
| | | | 435/5 |
| 2016/0311907 A1* | 10/2016 | Brogdon | C12N 9/90 |
| 2021/0106589 A1 | 4/2021 | Mizutani et al. | |

FOREIGN PATENT DOCUMENTS

| | | |
|---|---|---|
| EP | 1 356 816 | 10/2003 |
| EP | 1 944 029 | 7/2008 |
| EP | 2 842 549 | 3/2015 |
| EP | 3 290 424 | 3/2018 |
| EP | 3 391 888 | 10/2018 |
| JP | 2008-201712 | 9/2008 |
| JP | 2010-270112 | 12/2010 |
| JP | 2013-14610 | 1/2013 |
| JP | 2014-513714 | 6/2014 |
| JP | 2014-193898 | 10/2014 |
| JP | 2015-54822 | 3/2015 |
| JP | 2015-54851 | 3/2015 |
| TW | 201347792 | 12/2013 |
| WO | 2002/060446 | 8/2002 |
| WO | 2004/052342 | 6/2004 |
| WO | 2007/052592 | 5/2007 |
| WO | 2008/114859 | 9/2008 |
| WO | 2010/011814 | 1/2010 |
| WO | 2012/144592 | 10/2012 |
| WO | 2012/160352 | 11/2012 |
| WO | WO 2016/175224 | * 3/2016 |
| WO | 2016/175224 | 11/2016 |

(Continued)

OTHER PUBLICATIONS

International Search Report dated Feb. 19, 2019 in International (PCT) Application No. PCT/JP2018/042220 with English-language translation
Translation of The International Preliminary Report on Patentability dated May 28, 2020 in International (PCT) Application No. PCT/JP2018/042220.
Baertschi et al., "A Critical Assessment of the ICH Guideline on Photostability Testing of New Drug Substances and Products (Q1B): Recommendation for Revision," Journal of Pharmaceutical Sciences, Jul. 2010, vol. 99, No. 7, pp. 2934-2940.
Thoma et al., "Photostabilization of drugs in dosage forms without protection from packaging materials," International Journal of Pharmaceutics, 1991, vol. 67, pp. 169-175.

(Continued)

*Primary Examiner* — Marcos L Sznaidman
(74) *Attorney, Agent, or Firm* — WENDEROTH, LIND & PONACK, L.L.P.

(57) ABSTRACT

The present invention provides a preparation that is minimally colored through irradiation with light by coating a preparation containing a compound represented by formula (I) or a pharmaceutically acceptable salt thereof, or a crystal thereof with a light stabilizing substance and a polymer, particularly with one or more of titanium oxide and talc used as the light stabilizing substance and hypromellose used as the polymer.

14 Claims, 1 Drawing Sheet

(56) References Cited

FOREIGN PATENT DOCUMENTS

WO  2016/204291  12/2016
WO  2017/104691   6/2017

OTHER PUBLICATIONS

Taiwanese Office Action dated May 11, 2022 in Taiwanese Patent Application No. 107140226
Written Statement filed Jul. 9, 2021 in corresponding Japanese Patent Application No. 2020-18408, with English language translation.
Jinjiang Li et al., "Lubricants in Pharmaceutical Solid Dosage Forms," *Lubricants*, 2014, 2:21-43.

* cited by examiner

PHARMACEUTICAL PREPARATION EXCELLENT IN LIGHT STABILITY AND DISSOLUTION PROPERTY

TECHNICAL FIELD

The present invention relates to a preparation containing a polycyclic pyridone compound. It relates to a solid preparation containing a polycyclic pyridone compound that is coated with a light stabilizing substance and a polymer and is not colored when irradiated with light, and more specifically, it relates to a solid preparation containing a polycyclic pyridone compound that contains, as a light stabilizing substance, one or more substance selected from the group consisting of a food tar dye, a food laked tar dye, a natural food dye, iron oxide, titanium oxide and talc, contains hypromellose as a polymer and is not colored when irradiated with light.

BACKGROUND ART

Influenza is an acute respiratory infectious disease caused by infection with influenza virus. In Japan, there are millions of reports of patients with influenza-like diseases every winter, and influenza is accompanied with high morbidity and high mortality. It is particularly a significant disease in high risk populations such as the infants and the aged, a frequency of complications of pneumonia is high in the aged, and death with influenza is occupied in many cases.

As anti-influenza drugs, Symmetrel (tradename: Amantadine) and Flumadine (tradename: Rimantadine) inhibiting virus uncoating process, and neuraminidase inhibitors suppressing budding/release of the virus from a cell such as Oseltamivir (tradename: Tamiflu) and Zanamivir (tradename: Relenza) are known. However, since problems of appearance of resistant strains and adverse effects, and worldwide epidemic of a new-type influenza virus having high pathogenicity and mortality are feared, development of an anti-influenza drug having a novel mechanism has been desired.

Since a cap-dependent endonuclease which is an influenza virus-derived enzyme is essential for virus proliferation, and has the virus-specific enzymatic activity which is not possessed by a host, it is believed that the endonuclease is suitable for a target of an anti-influenza drug.

As a compound inhibiting the cap-dependent endonuclease, a compound represented by formula (II) is described in Patent Literature 1, and this compound is useful as a compound having antiviral activity, particularly, having inhibitory activity for influenza virus proliferation.

[Formula 1]

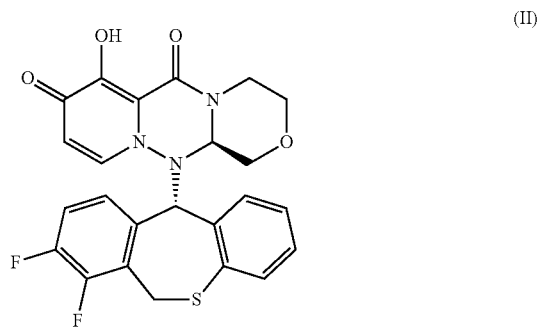

(II)

When the compound represented by formula (II) is administered (for example, orally administered) to a living body, it is necessary to provide a compound that is more efficiently absorbed into the body to show a high pharmacological effect and to shorten time to alleviation of influenza symptoms. To achieve these purposes, a compound represented by formula (I), that is a prodrug of the compound represented by formula (II), is provided. The compound represented by formula (I) is also disclosed in Patent Literature 1.

[Formula 2]

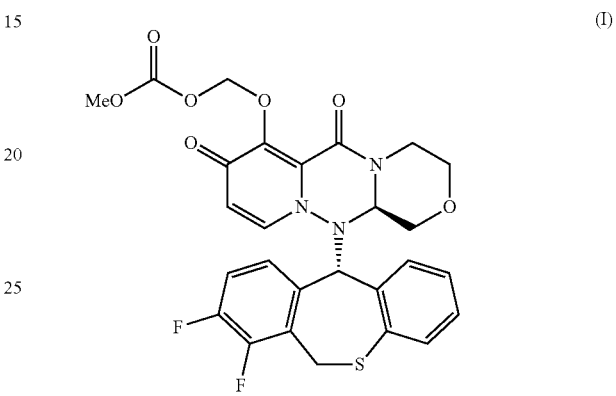

(I)

Patent Literature 1 does not, however, disclose a specific preparation of the compound represented by formula (I).

Patent Literatures 5 to 7 disclose preparations improved in a dissolution property. A compound used in each of Patent Literatures 5 to 7 is, however, largely different from the compound represented by formula (I) in the chemical structure, and it is unclear whether formulation described in each of Patent Literatures 5 to 7 can improve the dissolution property of the compound represented by formula (I), which is neither disclosed nor suggested. Besides, there is a possibility that a large amount of related substance may be generated depending on an additive for improving the dissolution property.

Furthermore, Patent Literatures 2 to 4 describe that when a preparation colored through light irradiation is coated with titanium oxide, the coloring of the preparation can be reduced. It is, however, varied, depending on a compound, whether a preparation is colored through light irradiation, and it is unclear whether the preparation containing the compound represented by formula (I) is colored, which is neither disclosed nor suggested.

CITATION LIST

Patent Literature

[Patent Literature 1] International Publication No. WO2016/175224
[Patent Literature 2] Japanese Patent Laid-Open No. 2013-14610
[Patent Literature 3] International Publication No. WO2002/060446
[Patent Literature 4] International Publication No. WO2007/052592
[Patent Literature 5] Japanese Patent Laid-Open No. 2010-270112

[Patent Literature 6] International Publication No. WO2004/052342

[Patent Literature 7] International Publication No. WO2012/144592

SUMMARY OF INVENTION

Technical Problem

An object of the present invention is to find a preparation that is not colored through light irradiation and contains a compound represented by formula (I), and further to provide a preparation in which a dissolution property of the compound represented by formula (I) is improved from the preparation.

Solution to Problem

The present inventors have found that when a preparation containing a compound represented by formula (I) is irradiated with light, the preparation itself is colored. Besides, the inventors have found that the compound represented by formula (I) has too low solubility to obtain a desired dissolution property.

In order to solve the above-described problems, the present inventors have made earnest studies resulting in finding that when a preparation containing a compound represented by formula (I) is coated with a light stabilizing substance and a polymer, the preparation is minimally colored through light irradiation, and thus, the present invention was accomplished. Besides, although the compound represented by formula (I) has too low solubility to obtain a desired dissolution property, the inventors have studied various disintegrating agents to find a disintegrating agent that generates a small amount of a related substance and can improve the dissolution property, and thus the present invention was accomplished. Hereinafter, a preparation thus accomplished by the present invention is sometimes referred to as the "present preparation".

Specifically, the present invention relates to the following;
(1) A solid preparation comprising a compound represented by formula (I);

[Formula 3]

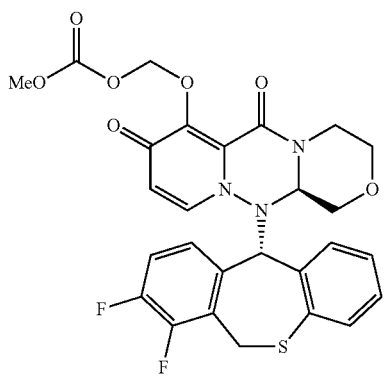

(I)

or a pharmaceutically acceptable salt thereof, which comprises a coating layer containing a light-stabilizing substance and a polymer;
(2) the solid preparation according to (1) above, wherein the light-stabilizing substance in the coating layer is one or more substance selected from the group consisting of edible tar dye, edible lake tar dye, edible natural dye, ferric oxide, titanium oxide and talc;
(3) the solid preparation according to (1) above, wherein the light-stabilizing substance in the coating layer is one or more substance selected from the group consisting of Food Red No. 2, Food Red No. 3, Food Red No. 102, Food Red No. 104, Food Red No. 105, Food Red No. 106, Food Yellow No. 4, Food Yellow No. 5, Food Green No. 3, Food Blue No. 1, Food Blue No. 2, Food Red No. 3 aluminum lake, Food Yellow No. 4 aluminum lake, Food Yellow No. 5 aluminum lake, Food Blue No. 1 aluminum lake, Food Blue No. 2 aluminum lake, carmine, sodium copper chlorophyllin, copper chlorophyll, red oxide, red ferric oxide, yellow ferric oxide, black iron oxide, yellow oxide of iron, titanium oxide and talc;
(4) the solid preparation according to (3) above, wherein the light-stabilizing substance in the coating layer is one or more substance selected from the group consisting of red ferric oxide, yellow ferric oxide, black iron oxide, yellow oxide of iron, titanium oxide and talc;
(5) the solid preparation according to (4) above, wherein the light-stabilizing substance in the coating layer is titanium oxide and/or talc;
(6) a solid preparation comprising a compound represented by formula (I):

[Formula 4]

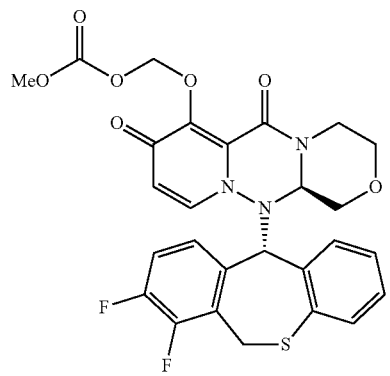

(I)

or a pharmaceutically acceptable salt thereof, which comprises a coating layer containing one or more substance selected from the group consisting of Food Red No. 2, Food Red No. 3, Food Red No. 102, Food Red No. 104, Food Red No. 105, Food Red No. 106, Food Yellow No. 4, Food Yellow No. 5, Food Green No. 3, Food Blue No. 1, Food Blue No. 2, Food Red No. 3 aluminum lake, Food Yellow No. 4 aluminum lake, Food Yellow No. 5 aluminum lake, Food Blue No. 1 aluminum lake, Food Blue No. 2 aluminum lake, carmine, sodium copper chlorophyllin, copper chlorophyll, red oxide, red ferric oxide, yellow ferric oxide, black iron oxide, yellow oxide of iron, titanium oxide and talc, and a polymer;
(7) the solid preparation according to (6) above, which comprises the compound represented by formula (I) or the pharmaceutically acceptable salt thereof, and the coating layer containing titanium oxide and/or talc, and the polymer;

(8) the solid preparation according to any one of (1) to (7) above, wherein the polymer in the coating layer is one or more substance selected from the group consisting of a cellulosic polymer, an acrylic polymer and a vinyl polymer;

(9) the solid preparation according to any one of (1) to (7) above, wherein the cellulosic polymer in the coating layer is one or more substance selected from the group consisting of hypromellose, hydroxypropyl cellulose, carboxy methyl ethyl cellulose, hypromellose phthalate, hydroxypropyl methylcellulose acetate succinate and ethyl cellulose;

(10) the solid preparation according to (9) above, wherein the cellulosic polymer is hypromellose;

(11) the solid preparation according to any one of (1) to (7) above, wherein the acrylic polymer in the coating layer is one or more substance selected from the group consisting of methacrylic acid copolymer, amino alkyl methacrylate copolymer E and amino alkyl methacrylate copolymer IRS;

(12) the solid preparation according to any one of (1) to (7) above, wherein the vinyl polymer in the coating layer is one or more substance selected from the group consisting of polyvinyl alcohol, polyvinylpyrrolidone and polyvinyl alcohol·methyl methacrylate·acrylate copolymer;

(13) the solid preparation according to (12) above, wherein the vinyl polymer is polyvinyl alcohol;

(14) a solid preparation comprising a compound represented by formula (I):

[Formula 5]

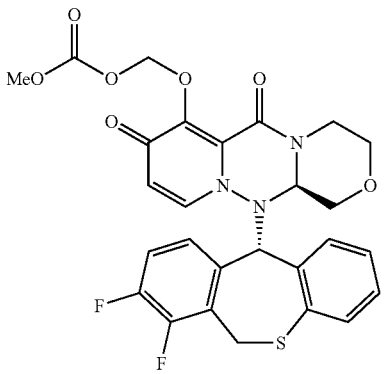

(I)

or a pharmaceutically acceptable salt thereof, which comprises a coating layer containing titanium oxide and/or talc, and hypromellose;

(15) the solid preparation according to any one of (1) to (14) above, further comprising a disintegrator;

(16) a solid preparation comprising a disintegrator, and a compound represented by formula (I):

[Formula 6]

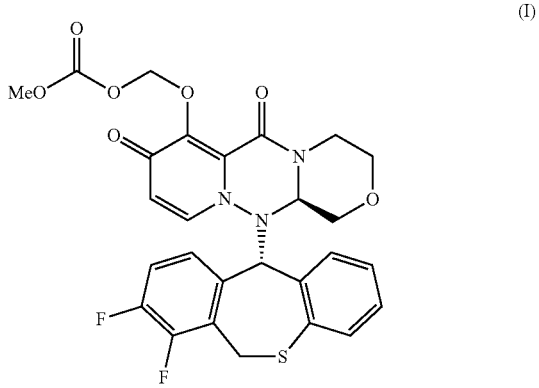 [SMILES: COC(=O)OCOc1c2n(ccc1=O)N([C@@H]1c3ccccc3SCc3c1ccc(F)c3F)[C@@H]1COCCN1C2=O]

(I)

or a pharmaceutically acceptable salt thereof;

(17) the solid preparation according to (15) or (16) above, wherein the disintegrator is one or more substance selected from the group consisting of low-substituted hydroxypropylcellulose, carmellose calcium, croscarmellose sodium, crospovidone, partly pregelatinized starch and sodium carboxymethyl starch;

(18) the solid preparation according to (17) above, wherein the disintegrator is low-substituted hydroxypropylcellulose or croscarmellose sodium;

(19) the solid preparation according to (18) above, wherein the disintegrator is croscarmellose sodium;

(20) the solid preparation according to (19) above, wherein the light stabilizing substance is titanium oxide and/or talc, and the polymer is hypromellose in the coating layer;

(21) the solid preparation according to any one of (1) to (20) above, wherein the color difference ΔE is not more than 13 at optical illumination of 1.2 million lux;

(22) a solid preparation comprising a light-stabilizing substance and a compound represented by formula (I):

[Formula 7]

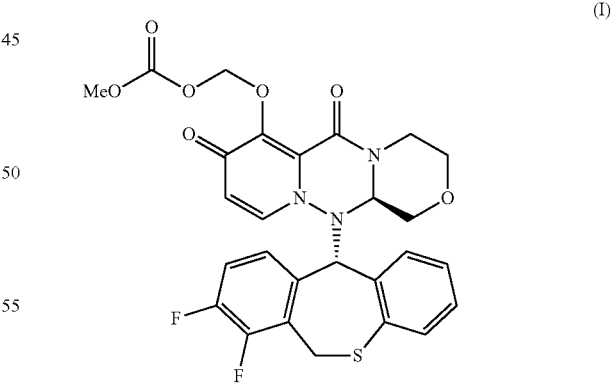

(I)

or a pharmaceutically acceptable salt thereof, and a color difference ΔE is not more than 13 at optical illumination of 1.2 million lux;

(23) the solid preparation according to (22) above, wherein the light-stabilizing substance is one or more substance selected from the group consisting of edible tar dye, edible lake tar dye, edible natural dye, ferric oxide, titanium oxide and talc;

(24) the solid preparation according to (23) above, wherein the light-stabilizing substance is titanium oxide and/or talc;

(25) the solid preparation according to any one of (1) to (24) above, which is packaged in an aluminum blister package;

(26) a solid preparation comprising a compound represented by formula (I):

[Formula 8]

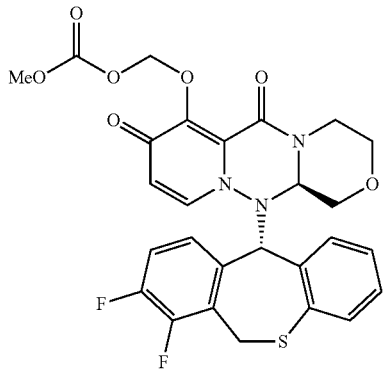

(I)

or a pharmaceutically acceptable salt thereof, which is packaged in an aluminum blister package;

(27) the solid preparation according to any one of (1) to (26) above, which is a granule or a tablet;

(28) the solid preparation according to any one of (1) to (27) above, wherein the release rate of the compound represented by formula (I) is not less than 80% after 45 minutes of initiation of dissolution test;

(29) a method for analyzing a degradation product in a solid preparation containing a compound represented by formula (I):

[Formula 9]

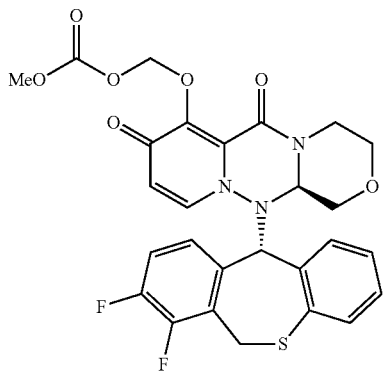

(I)

or a pharmaceutically acceptable salt thereof, wherein the method comprises the steps of:
a) performing chromatography of the solid preparation containing the compound represented by formula (I) or the pharmaceutically acceptable salt thereof used as a sample; and b) obtaining data on a content or a content rate of a compound represented by the formula (II):

[Formula 10]

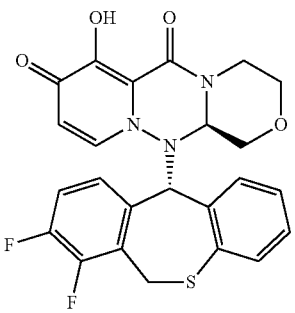

(II)

from chromatography data obtained in the step (a);

(30) a degradation product comprising a compound represented by formula (I):

[Formula 11]

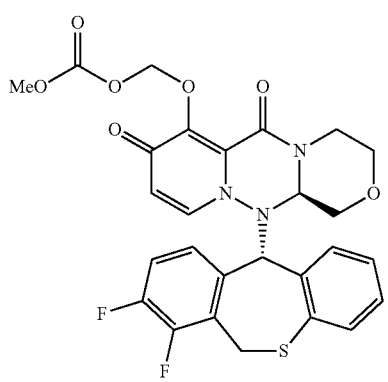

(I)

or a pharmaceutically acceptable salt thereof, which comprises a compound represented by formula (II):

[Formula 12]

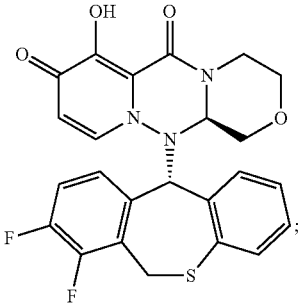

(II)

(31) the solid preparation according to any one of (1) to (28) above, which comprises a 10 mg, 20 mg, 40 mg or 80 mg compound represented by formula (I):

[Formula 13]

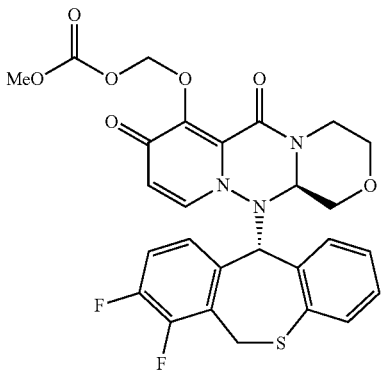

(I)

(32) the solid preparation according to any one of (1) to (28) above, which is used for shortening the duration infected with influenza;
(33) the solid preparation according to any one of (1) to (28) above, which is used for reducing the influenza virus.

Advantageous Effects of Invention

According to the present invention, even when a solid preparation having a coating layer containing a light stabilizing substance and a polymer, the solid preparation containing a compound represented by formula (I) or a pharmaceutically acceptable salt thereof is irradiated with light, color of the preparation is little varied from that at an initial stage of a test. Specifically, the present preparation of a color difference ΔE is preferably 13 or less.

DESCRIPTION OF EMBODIMENTS

Figure 1:
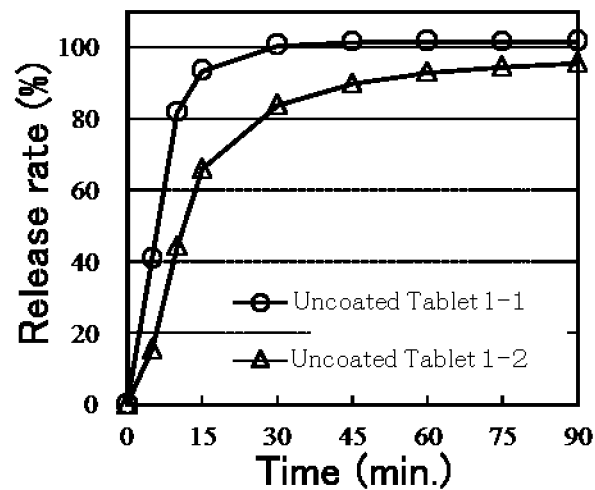
FIG. 1 illustrates dissolution behavior of a tablet using low substituted hydroxypropyl cellulose as a disintegrating agent.

As an active ingredient of the present preparation, a compound represented by formula (I) or a pharmaceutically acceptable salt thereof is used:

[Formula 14]

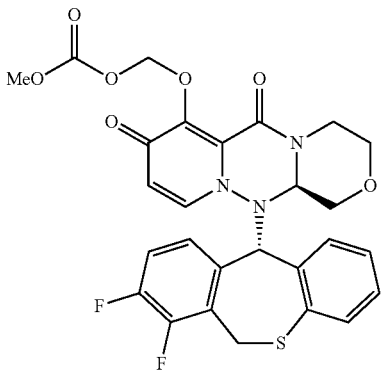

(I)

A method for producing the compound represented by formula (I) or a pharmaceutically acceptable salt thereof is disclosed in Patent Literature 1.

The compound represented by formula (I) or the pharmaceutically acceptable salt thereof is converted into a compound represented by formula (II) in a living body, and has an inhibitory activity on cap-dependent endonuclease. Accordingly, the compound represented by formula (I) or the pharmaceutically acceptable salt thereof is useful as an agent for treating and/or preventing influenza.

The compound represented by formula (I) or the pharmaceutically acceptable salt thereof is useful for symptoms and/or diseases induced by influenza virus. It is useful for treatment and/or prevention and symptom improvement of, for example, cold-like symptoms accompanied with fever, body chill, headache, muscle pain and general malaise, airway inflammation symptoms such as sore throat, nasal discharge, nasal congestion, cough and phlegm, gastrointestinal symptoms such as stomachache, vomiting and diarrhea, and complications accompanying secondary infection such as acute encephalopathy and pneumonia. In other words, the compound used in the present invention is useful for treatment and/or prevention of influenza virus infectious diseases.

The compound represented by formula (I) or the pharmaceutically acceptable salt thereof is useful for shortening time to alleviation of influenza symptoms. The disease duration of influenza can be shortened by, for example, about 20 to 40 hours or about 25 to 30 hours. Specifically, time necessary for improving "cough", "sore throat", "headache", "nasal congestion", "feverishness or body chill", "muscle or joint pain" and "fatigue" can be shortened. It is useful particularly for shortening the time necessary for improving "nasal congestion", "muscle or joint pain", "fatigue", "feverishness or body chill" and "headache". Besides, it is useful for shortening the time necessary for improving "nasal congestion" and "muscle or joint pain".

The compound represented by formula (I) or the pharmaceutically acceptable salt thereof has usefulness as a pharmaceutical. The compound represented by formula (I) or the pharmaceutically acceptable salt thereof is a prodrug having advantages that it has high oral absorption, good bio-availability and clearance and high distribution into lung, and hence can be an excellent pharmaceutical.

The compound represented by formula (I) or the pharmaceutically acceptable salt thereof exhibits high metabolic stability and oral absorption and good bio-availability and clearance. Besides, the compound represented by formula (I) or the pharmaceutically acceptable salt thereof is highly distributed into lung and has a long half-life. Furthermore, the compound represented by formula (I) or the pharmaceutically acceptable salt thereof has advantages that it has a high non-protein binding rate and low hERG channel inhibition or CYP inhibition, exhibits a CPE (cytopathic effect) inhibitory activity, and/or is negative in phototoxicity test, Ames test and genotoxicity test, or it does not have toxicity causing liver damage or the like. Accordingly, a pharmaceutical composition of the present invention can be an excellent pharmaceutical.

A dose of the compound represented by formula (I) or the pharmaceutically acceptable salt thereof is varied depending on an administration method, the age, the weight and the state of a patient and the type of disease, and in employing oral administration, a dose of usually about 0.05 mg to 3000 mg, preferably about 0.1 mg to 1000 mg, further preferably about 10 mg to 80 mg, and particularly preferably about 10 mg to 40 mg is administered to an adult per day dividedly if necessary. In employing parenteral administration, a dose of about 0.01 mg to 1000 mg, preferably about 0.05 mg to 500 mg, or about 1 mg to 80 mg is administered to an adult per day. Such a dose may be administered once or dividedly several times a day.

The compound represented by formula (I) or the pharmaceutically acceptable salt thereof can be used in combination with another drug or the like (hereinafter referred to as the combination drug) for purposes of enhancing the action of the compound or reducing the dose of the compound. For a disease of influenza, for example, it can be used in combination with a neuraminidase inhibitor (such as Oseltamivir, Zanamivir, Peramivir or Inavir), an RNA-dependent RNA polymerase inhibitor (such as Favipiravir), an M2 protein inhibitor (such as Amantadine), a PB2 cap-binding inhibitor (such as VX-787), an anti-HA antibody (such as MHAA4549A), or an immune agonist (such as nitazoxanide). In this case, administration periods of the compound and the combination drug employed in the present invention are not limited, and these may be simultaneously administered to a subject of administration, or may be administered with a time lag. Besides, the compound represented by formula (I) or the pharmaceutically acceptable salt thereof and the combination drug may be administered in the form of two or more preparations respectively containing active ingredients, or may be administered in the form of a single preparation containing all the active ingredients.

The dose of the combination drug can be appropriately selected based on a clinically employed dose. Besides, a blending ratio between the compound represented by formula (I) or the pharmaceutically acceptable salt thereof and the combination drug can be appropriately selected depending on the subject of administration, the administration route, the target disease, the symptoms, a combination therebetween and the like. When the subject of administration is, for example, a human, the combination drug may be used in an amount of 0.01 to 100 parts by weight based on 1 part by weight of the compound represented by formula (I) or the pharmaceutically acceptable salt thereof.

The compound represented by formula (I) or the pharmaceutically acceptable salt thereof can be a pharmaceutical less likely to cause adverse reactions because it is a virus-specific enzyme having high inhibitory activity against cap structure-dependent endonuclease and hence has effects of high selectivity and the like.

Now, a method for specifying a compound represented by formula (I) or a crystal thereof, or a compound represented by formula (II) will be described.

Numerical values mentioned for ranges herein and in the appended claims are approximate values unless otherwise specified. Variation of numerical values is caused by factors such as device calibration, device error, an impurity of a substance, a crystal size and a sample size.

The term "crystal" as used herein means a cyclic and anisotropic structure resulting from a structure in which atoms, ions, molecules or the like constituting a solid are regularly aligned. A degree of crystallinity of a crystal form can be measured any of various techniques including, for example, powder X-ray diffraction analysis, moisture adsorption/desorption analysis, differential scanning calorimetry, simultaneous thermogravimetric analysis, solution colorimetric analysis and solubility characteristics.

NMR analysis of a compound was performed at 300 MHz using DMSO-$d_6$ and $CDCl_3$.

Measurement of Powder X-Ray Diffraction Pattern

In accordance with X-ray Powder Diffraction Method described in General Tests of The Japanese Pharmacopoeia, a crystal obtained in each example was subjected to powder X-ray diffraction analysis. Analysis conditions are as follows:

(Apparatus)

MiniFlex 600 RINT-TTR III manufactured by Rigaku Corporation (Operation Method)

Detector: high-speed one-dimensional detector (D/Tec Ultra 2) and variable knife edge Measurement method: reflection method Type of light source: Cu tube Wavelength used: CuKα ray Tube current: 10 mA or 15 mA Tube voltage: 30 Kv or 40 Kv Sample plate: aluminum or glass Incident angle (θ) of X-rays: 3-40°, Sampling width: 0.01° or Incident angle (θ) of X-rays: 4-40°, Sampling width: 0.02°

In general, an error occurs in a range of ±0.2° in a diffraction angle (2θ) in the powder X-ray diffraction, and therefore, the value of the diffraction angle embraces values falling in the range of about ±0.2°. Accordingly, not only a crystal completely the same in the diffraction angle at a peak in the powder X-ray diffraction but also a crystal the same in the diffraction angle at a peak with an error of about ±0.2° is embraced in the present invention.

A content of the compound represented by formula (I) or the pharmaceutically acceptable salt thereof in the present preparation is 1 to 80% by weight, preferably 5 to 75% by weight, and more preferably 10 to 70% by weight based on the total amount of the preparation.

The present preparation contains a light stabilizing substance. Herein, the light stabilizing substance may be any additive as long as it can stabilize against light, the compound represented by formula (I) or the pharmaceutically acceptable salt thereof, and can prevent color change of the preparation, and those described in The Japanese Pharmacopoeia, The Japanese Pharmaceutical Codex, The Japanese Pharmaceutical Excipients, and The Japan's Specifications and Standards for Food Additives can be used.

Examples of the light stabilizing substance include a light-shielding substance having a light-shielding effect for shielding light and a light-absorbing substance having an effect for absorbing light. Specific examples include a food tar dye, a food laked tar dye, a natural food dye, iron oxide, titanium oxide and talc. Preferable examples include Food Red No. 2, Food Red No. 3, Food Red No. 102, Food Red No. 104, Food Red No. 105, Food Red No. 106, Food Yellow No. 4, Food Yellow No. 5, Food Green No. 3, Food Blue No. 1, Food Blue No. 2, Food Red No. 3 aluminum lake, Food Yellow No. 4 aluminum lake, Food Yellow No. 5 aluminum lake, Food Blue No. 1 aluminum lake, Food Blue No. 2 aluminum lake, carmine, copper chlorophyllin sodium, copper chlorophyll, colcothar, ferric oxide, yellow ferric oxide, black iron oxide, yellow iron oxide, titanium oxide and talc. Titanium oxide and talc of the light-shielding substances, and ferric oxide, yellow ferric oxide, black iron oxide and yellow iron oxide of the light-absorbing substances are more preferred, and titanium oxide and talc of the light-shielding substances are particularly preferred.

The light stabilizing substance of the present preparation may be blended in the preparation or may be coated on a surface of the preparation, and preferably, the light stabilizing substance is coated on a surface of the preparation, namely, the light stabilizing substance is contained in what is called a coating layer. When the light stabilizing substance is contained in the coating layer of the preparation, it absorbs or shields light from the outside of the preparation, and hence, the light stability of the compound represented by formula (I) contained in the preparation can be improved or the color change of the preparation can be prevented.

A content of the light stabilizing substance in the present preparation may be any amount with which the compound represented by formula (I) or the pharmaceutically acceptable salt thereof is stabilized against light. Specifically, among the light stabilizing substances, a content of the light-shielding substance such as titanium oxide or talc is 0.00075 to 0.075 mg, preferably 0.001 to 0.05 mg, and more preferably 0.0015 to 0.03 mg per $mm^2$ of a surface area of the preparation.

The present preparation contains a polymer. Herein, those described in The Japanese Pharmacopoeia, The Japanese Pharmaceutical Codex, The Japanese Pharmaceutical Excipients, and The Japan's Specifications and Standards for Food Additives can be used as the polymer. Specific examples include cellulose-based polymers such as hypromellose (hydroxypropyl methylcellulose), polyvinyl alcohol, ethyl cellulose, carboxymethyl ethyl cellulose, carmellose, carmellose sodium, hydroxyethyl cellulose, hydroxyethyl methyl cellulose, hydroxypropyl cellulose, hydroxypropyl methyl cellulose acetate succinate, hydroxypropyl methyl cellulose phthalate, and a fumaric acid/stearic acid/polyvinyl acetal diethylamino acetate/hydroxypropyl methyl cellulose mixture; acrylic-based polymers such as an ethyl acrylate/methyl methacrylate copolymer dispersion, an aminoalkyl methacrylate copolymer, a methacrylic acid copolymer, a 2-methyl-5-vinylpyridine methyl acrylate/methacrylic acid copolymer, a dried methacrylic acid copolymer, and a dimethyl aminoethyl methacrylate/methyl methacrylate copolymer; vinyl-based polymers such as polyvinyl pyrrolidone, crospovidone, a carboxyvinyl polymer, polyvinyl acetal diethylamino acetate, polyvinyl alcohol, a polyvinyl alcohol/methyl methacrylate/acrylic acid polymer, and a polyvinyl alcohol copolymer; and carnauba wax, stearyl alcohol, shellac and cetanol, among which hypromellose (hydroxypropyl methylcellulose) is preferred.

The polymer of the present preparation may be blended in the preparation, or may be coated on the surface of the preparation, and preferably, the polymer is used as what is called a coating agent for coating the surface of the preparation to form the coating layer. When the polymer is contained in the coating layer of the preparation, it can coat, together with the light stabilizing substance, the surface of the preparation, and hence, the light stability of the compound represented by formula (I) contained in the preparation can be improved, and the color change of the preparation can be prevented.

A content of the polymer in the coating layer herein may be any amount as long as the light stabilizing substance can be coated on the surface of the preparation.

The present preparation may contain a disintegrating agent. Any disintegrating agents described in The Japanese Pharmacopoeia, The Japanese Pharmaceutical Codex, The Japanese Pharmaceutical Excipients, and The Japan's Specifications and Standards for Food Additives can be used as the disintegrating agent, and in using some kinds of disintegrating agents, the amount of a related substance containing the compound represented by formula (II) may be increased in some cases. Specific examples include croscarmellose sodium, crospovidone, carmellose calcium, carboxymethyl starch sodium, and low substituted hydroxypropyl cellulose, among which croscarmellose sodium is preferred.

A content of the disintegrating agent in the present preparation is 0.5 to 20% by weight, preferably 0.75 to 15% by weight, and more preferably 1 to 10% by weight based on the total amount of the preparation. When the content is smaller, there is a possibility that a resultant solid preparation, particularly in the form of a tablet, is not sufficiently disintegrated.

The present preparation may contain an excipient. Any excipients described in The Japanese Pharmacopoeia, The Japanese Pharmaceutical Codex, The Japanese Pharmaceutical Excipients, and The Japan's Specifications and Standards for Food Additives can be used as the excipient. Specific examples include sugar alcohols such as D-mannitol, xylitol, sorbitol, maltitol, lactitol and oligosaccharide alcohol, sugars such as xylose, glucose, fructose, maltose, lactose, sucrose, isomerized sugar, syrup, purified white sugar, white sugar, purified sucrose spherical granule, anhydrous lactose, and sucrose/starch spherical granule, semi-digested starch, glucose hydrate, powdered sugar, crystalline cellulose, microcrystalline cellulose, pullulan, 6-cyclodextrin, aminoethyl sulfonic acid, candy powder, sodium chloride, citric acid, sodium citrate, glycine, calcium gluconate, L-glutamine, tartaric acid, potassium hydrogen tartrate, ammonium carbonate, dextran 40, dextrin, calcium lactate, povidone, macrogol (polyethylene glycol) 1500, macrogol 1540, macrogol 4000, macrogol 6000, anhydrous citric acid, DL-malic acid, sodium hydrogen phosphate, potassium dihydrogen phosphate, sodium dihydrogen phosphate, L-aspartic acid, alginic acid, carmellose sodium, hydrated silicon dioxide, crospovidone, calcium glycerophosphate, magnesium aluminosilicate, calcium silicate, magnesium silicate, light anhydrous silicic acid, synthetic aluminum silicate, flour, wheat starch, wheat germ flour, rice flour, rice starch, cellulose acetate phthalate, titanium oxide, magnesium oxide, dihydroxyaluminum aminoacetate, tribasic calcium phosphate, talc, calcium carbonate, magnesium carbonate, precipitated calcium carbonate, natural aluminum silicate, corn starch, granulated corn starch, potato starch, hydroxypropyl cellulose, hydroxypropyl starch, anhydrous calcium hydrogen phosphate, granulated anhydrous calcium hydrogen phosphate and calcium dihydrogen phosphate, among which sugars and crystalline cellulose are preferred, and lactose and crystalline cellulose are further preferred.

A content of the excipient in the present preparation is 10 to 90% by weight, preferably 15 to 87.5% by weight and more preferably 20 to 85% by weight based on the total amount of the preparation.

The present preparation may contain a binder. Any binders described in The Japanese Pharmacopoeia, The Japanese Pharmaceutical Codex, The Japanese Pharmaceutical Excipients, and The Japan's Specifications and Standards for Food Additives can be used as the binder. Specific examples include hydroxypropyl cellulose, corn starch, pregelatinized starch, partially pregelatinized starch, gum arabic, gum arabic powder, gelatin, agar, dextrin, pullulan, polyvinyl pyrrolidone, polyvinyl alcohol, crystalline cellulose, methyl cellulose, ethyl cellulose, carboxymethyl ethyl cellulose, carmellose, carmellose sodium, hydroxyethyl cellulose, hydroxyethyl methyl cellulose, hydroxypropyl cellulose and hypromellose, among which polyvinyl pyrrolidone is preferred.

A content of the binder in the present preparation is 0.1 to 20% by weight, preferably 0.25 to 15% by weight, and more preferably 0.5 to 10% by weight based on the total amount of the preparation.

The present preparation may contain a lubricant. Any lubricants described in The Japanese Pharmacopoeia, The Japanese Pharmaceutical Codex, The Japanese Pharmaceutical Excipients, and The Japan's Specifications and Standards for Food Additives can be used as the lubricant. Specific examples include metal stearate, sucrose fatty acid ester, talc, hydrated silicon dioxide and sodium stearyl fumarate, among which sodium stearyl fumarate is preferred.

A content of the lubricant is usually 0.05 to 10% by weight, preferably 0.075 to 7.5% by weight, and more preferably 0.1 to 5% by weight based on the total amount of the preparation.

In order to efficiently perform a coating operation of the polymer, a plasticizer or an aggregation inhibitor may be contained in the coating agent for the coating layer of the present preparation, and those described in The Japanese Pharmacopoeia, The Japanese Pharmaceutical Codex, The Japanese Pharmaceutical Excipients, and The Japan's Specifications and Standards for Food Additives can be used. Specific examples include triethyl citrate, glycerin fatty acid ester, sucrose fatty acid ester, castor oil, triacetin and talc. On the other hand, when macrogol (polyethylene glycol) is contained, the amount of the related substance may be increased in some cases.

The present preparation may contain a dye or a colorant, and any dyes described in The Japanese Pharmacopoeia, The Japanese Pharmaceutical Codex, The Japanese Pharmaceutical Excipients, and The Japan's Specifications and Standards for Food Additives can be used. The dye may be contained either in the tablet or in the coating layer. Specific examples of the dye include iron oxide, a tar dye and a natural dye. Examples of the iron oxide include ferric oxide, yellow iron oxide, yellow ferric oxide and black iron oxide. Examples of the tar dye include Food Yellow No. 4 aluminum lake, Food Blue No. 1 aluminum lake, Food Red No. 3 aluminum lake, Food Blue No. 1, Food Blue No. 2, Food Yellow No. 4, Food Yellow No. 5, Food Red No. 102, Food Red No. 2 and Food Red No. 3. Examples of the natural dye include a turmeric extract, 6-carotene, a carotene solution, sodium copper chlorophyllin, copper chlorophyll, a naked barley green leaf extract powder, a dried powder of green juice of naked barley green leaves, a naked barley green leaf extract, titanium oxide and talc. Examples of the dye include those used as the light stabilizing substance.

The present preparation may contain another additive if necessary in addition to those described above, and any additives described in The Japanese Pharmacopoeia, The Japanese Pharmaceutical Codex, The Japanese Pharmaceutical Excipients, and The Japan's Specifications and Standards for Food Additives can be used. Besides, a content of such an additive may be an arbitrary rate. Specific examples of the additive used in addition to those described above include a perfume, a fluidizing agent and a flavoring agent.

Specific examples of the perfume include an orange extract, orange oil, caramel, camphor, cinnamon oil, spearmint oil, a strawberry extract, a chocolate extract, cherry flavor, spruce oil, pine oil, peppermint oil, vanilla flavor, a bitter extract, fruit flavor, a peppermint extract, mixture flavor, mint flavor, menthol, a lemon powder, lemon oil and rose oil.

Specific examples of the fluidizing agent include hydrated silicon dioxide, light anhydrous silicic acid, crystalline cellulose, synthetic aluminum silicate and talc.

Specific examples of the flavoring agent include aspartame, sucralose, glycine, sodium chloride, magnesium chloride, hydrochloric acid, dilute hydrochloric acid, citric acid and a salt thereof, anhydrous citric acid, L-glutamic acid and a salt thereof, succinic acid and a salt thereof, acetic acid, tartaric acid and a salt thereof, sodium hydrogen carbonate, fumaric acid and a salt thereof, malic acid and a salt thereof, glacial acetic acid, disodium inosinate and honey.

The present preparation may be a solid preparation. Specifically, it may be a granule, a fine granule, a tablet, a powder, a capsule, a pill or the like, and is preferably a granule or a tablet. A dose of the compound represented by formula (I) contained in the solid preparation is not especially limited, and specifically is preferably 10 mg, 20 mg, 40 mg or 80 mg. In this case, 10 mg represents the range of 9.0 to 11.0 mg, preferably 9.5 to 10.5 mg, 20 mg represents the range of 18.0 to 22.0 mg, preferably 19.0 to 21.0 mg, 40 mg represents 36.0 to 44.0 mg, preferably 38.0 to 42.0 mg, 80 mg represents the range of 72.0 to 88.0 mg, preferably 76.0 to 84.0 mg.

A method for producing a granule of the present preparation is not especially limited, and specifically is a method in which the active ingredients and additives such as a disintegrating agent and an excipient are mixed to produce a mixed powder, and the mixed powder is granulated, and is preferably a wet granulation method in which granulation is performed with water, water containing a binder or a solvent added, a dry granulation method in which compression molding is performed without using water, or a melt granulation method. As a machine to be used for mixing the active ingredients, additives and the like, a V-shaped mixer or a container blender can be used. Besides, as a machine to be used for granulation, a wet pellet mill, a fluidized bed granulator, a stirring granulator, a dry crushing granulator or a melt extrusion granulator can be used. In the case of wet granulation, the amount of water to mixture during the wet granulation is 1 to 50%, preferably 5 to 47.5%, more preferably 10 to 45%.

A method for producing a tablet of the present preparation is not especially limited, and specifically is a tableting method in which a granule is produced by the above-described method, a disintegrating agent and a lubricant are mixed with the granule, and the thus obtained mixed granule is tableted with a tableting machine. As a machine to be used for mixing the active ingredients, additives and the like, a V-shaped mixer or a container blender can be used. Besides, as the tableting machine, a single punch tableting machine, a rotary tableting machine or the like can be used.

After producing the granule or the tablet of the present preparation as described above, the resultant granule or the tablet may be coated with the light stabilizing substance and the polymer to form the coating layer thereon in some cases. When the coating layer is to be formed on the granule, a fluidized bed granulation coating machine, a fluidized bed rolling coating machine or the like can be used. When the coating layer is to be formed on the tablet, a pan coating machine, a vented coating machine or the like can be used. In forming the coating layer using the light stabilizing substance and the polymer on the surface of the preparation, the light stabilizing substance and the polymer are dissolved or suspended in water or a solvent such as ethanol to prepare a coating solution. With the granule or the tablet caused to flow in the coating machine, the coating solution is sprayed onto the granule or the tablet, and the resultant is dried to form the coating layer.

Moreover, the release rate of compound represented by formula (I) in the present preparation is not less than 70%, preferably not less than 75%, more preferably not less than 80% after 45 minutes of initiation of dissolution test.

When the present preparation is irradiated with light, the amount of a related substance is minimally increased from the start of an experiment, and a color difference of the preparation is minimally changed, and in particular, the color difference ΔE of the preparation is minimally changed from the start of the experiment. Specifically, when the preparation is put in an exposure apparatus to be irradiated with light in a total irradiation amount of 1.2 million lux·hr, the color difference of the preparation is Δ13 or less.

Besides, the present invention embraces a method for analyzing a degradation product in a solid preparation containing a compound represented by formula (I) or a pharmaceutically acceptable salt thereof:

[Formula 15]

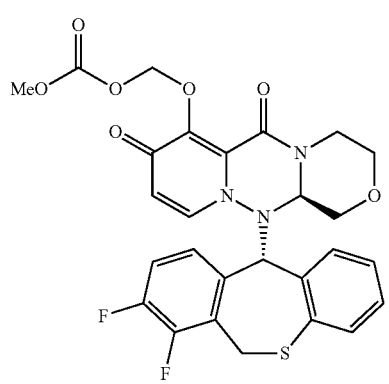

(I)

the method including the steps of; (a) performing chromatography of the compound represented by formula (I) or the pharmaceutically acceptable salt thereof used as a sample; and (b) obtaining, from chromatography data obtained in the step (a), data on a content or a content rate of a compound represented by formula (II);

[Formula 16]

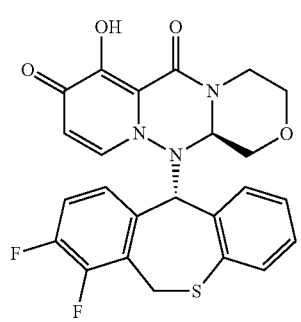

(II)

For example, an amount (a content or a content rate) of a related substance containing the compound represented by formula (II) can be measured by high performance liquid chromatography. At this point, the compound represented by formula (II) can be used as a reference in measuring the related substance. A content or a content rate of the compound represented by formula (II) can be calculated based on a peak area of chromatography data. For example, for measurement of the compound represented by formula (I) and the compound represented by formula (II) by the chromatography, a wavelength of 260 nm can be used as a measurement wavelength. As the content rate, a rate in the whole preparation, a rate to the compound represented by formula (I), a rate to a sum of the compound represented by formula (I) and the compound represented by formula (II) or the like can be used. Furthermore, when the amount of the compound represented by formula (II) is reduced, there is a possibility that the color difference ΔE of the preparation can be reduced.

Incidentally, a principal related substance of the compound represented by formula (I) hay the following structure:

[Formula 17]

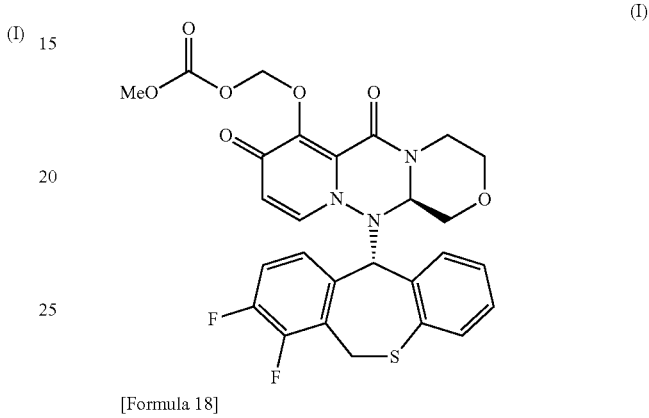

(I)

[Formula 18]

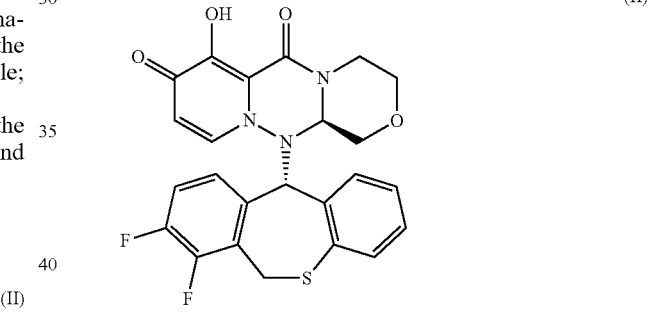

(II)

A content of the compound represented by formula (I) in a tablet may be any content as long as a patient can easily take the tablet and the tablet can be produced, and is 1 to 400 mg, preferably 1.25 to 350 mg, and more preferably 2.5 to 300 mg per tablet.

The present invention is a solid preparation having a coating layer containing a light stabilizing substance and a polymer, and containing a compound represented by formula (I) or a pharmaceutically acceptable salt thereof.

Preferably, it is a solid preparation using, as the light stabilizing substance contained in the coating layer, a substance that shields or absorbs light.

The light stabilizing substance is preferably one or more substance selected from the group consisting of a food tar dye, a food laked tar dye, a natural food dye, iron oxide, titanium oxide and talc.

The light stabilizing substance is preferably a light absorbing substance such as Food Red No. 2, Food Red No. 3, Food Red No. 102, Food Red No. 104, Food Red No. 105, Food Red No. 106, Food Yellow No. 4, Food Yellow No. 5, Food Green No. 3, Food Blue No. 1, Food Blue No. 2, Food Red No. 3 aluminum lake, Food Yellow No. 4 aluminum lake, Food Yellow No. 5 aluminum lake, Food Blue No. 1 aluminum lake, Food Blue No. 2 aluminum lake, carmine, copper chlorophyllin sodium, copper chlorophyll, colcothar, ferric oxide, yellow ferric oxide, black iron oxide or yellow iron oxide, or a light shielding substance such as titanium oxide, talc or silicon dioxide.

In particular, one or more substance selected from the group consisting of ferric oxide, yellow ferric oxide, black iron oxide, yellow iron oxide, titanium oxide and talc are preferred.

Furthermore, titanium oxide and/or talc are preferred.

Besides, the polymer contained in the coating layer is preferably one or more substance selected from the group consisting of a cellulose-based polymer, an acrylic-based polymer and a vinyl-based polymer.

The cellulose-based polymer is preferably one or more substance selected from the group consisting of hypromellose, hydroxypropyl cellulose, carboxymethyl ethyl cellulose, hypromellose phthalate, hydroxypropyl methyl cellulose acetate succinate and ethyl cellulose.

In particular, hypromellose is preferred.

The acrylic-based polymer is preferably one or more substance selected from the group consisting of a methacrylic acid copolymer, an aminoalkyl methacrylate copolymer E and an aminoalkyl methacrylate copolymer RS.

The vinyl-based polymer is preferably one or more substance selected from polyvinyl alcohol, polyvinyl pyrrolidone, crospovidone and a polyvinyl alcohol/methyl methacrylate/acrylic acid copolymer.

It is preferable that the light stabilizing substance contained in the coating layer is titanium oxide and talc and that the polymer is hypromellose.

Preferable aspects will now be described.

One aspect is a solid preparation having a coating layer containing a light stabilizing substance shielding or absorbing light and a polymer, and containing a compound represented by formula (I) or a pharmaceutically acceptable salt thereof, and particularly preferably a solid preparation having a coating layer containing titanium oxide, talc and a polymer, and containing a compound represented by formula (I) or a pharmaceutically acceptable salt thereof.

Another aspect is a solid preparation having a coating layer containing a light stabilizing substance and one or more polymers selected from the group consisting of a cellulose-based polymer, an acrylic-based polymer and a vinyl-based polymer, and containing a compound represented by formula (I) or a pharmaceutically acceptable salt thereof, preferably a solid preparation having a coating layer containing a light stabilizing substance shielding or absorbing light and one or more polymers selected from the group consisting of a cellulose-based polymer, an acrylic-based polymer and a vinyl-based polymer, and containing a compound represented by formula (I) or a pharmaceutically acceptable salt thereof, and more preferably a solid preparation having a coating layer containing one or more light stabilizing substances selected from the group consisting of a food tar dye, a food laked tar dye, a natural food dye, iron oxide, titanium oxide and talc, and one or more polymers selected from the group consisting of a cellulose-based polymer, an acrylic-based polymer and a vinyl-based polymer, and containing a compound represented by formula (I) or a pharmaceutically acceptable salt thereof, and particularly preferably having a coating layer containing titanium oxide and talc, and one or more polymers selected from the group consisting of a cellulose-based polymer, an acrylic-based polymer and a vinyl-based polymer, and containing a compound represented by formula (I) or a pharmaceutically acceptable salt thereof.

A still another aspect is a solid preparation having a coating layer containing a light stabilizing substance and a cellulose-based polymer, and containing a compound represented by formula (I) or a pharmaceutically acceptable salt thereof, preferably having a coating layer containing a light stabilizing substance shielding or absorbing light and a cellulose-based polymer, and containing a compound represented by formula (I) or a pharmaceutically acceptable salt thereof, and more preferably a solid preparation having a coating layer containing one or more light stabilizing substances selected from the group consisting of a food tar dye, a food laked tar dye, a natural food dye, iron oxide, titanium oxide and talc, and a cellulose-based polymer, and containing a compound represented by formula (I) or a pharmaceutically acceptable salt thereof, and particularly preferably having a coating layer containing titanium oxide, talc and a cellulose-based polymer, and containing a compound represented by formula (I) or a pharmaceutically acceptable salt thereof.

Still another aspect is a solid preparation having a coating layer containing a light stabilizing substance and hypromellose, and containing a compound represented by formula (I) or a pharmaceutically acceptable salt thereof, preferably a solid preparation having a coating layer containing a light stabilizing substance shielding or absorbing light and hypromellose, and containing a compound represented by formula (I) or a pharmaceutically acceptable salt thereof, and more preferably a solid preparation having a coating layer containing one or more light stabilizing substances selected from the group consisting of a food tar dye, a food laked tar dye, a natural food dye, iron oxide, titanium oxide and talc, and hypromellose, and containing a compound represented by formula (I) or a pharmaceutically acceptable salt thereof, and particularly preferably having a coating layer containing titanium oxide, talc and hypromellose, and containing a compound represented by formula (I) or a pharmaceutically acceptable salt thereof.

Even when the present preparation is packaged in a light absorbing or shielding material, a color difference of the preparation caused through irradiation with light of a total irradiation amount of 1.2 million lux·hr is Δ13 or less. Besides, even when a preparation containing merely the compound represented by formula (I) is packaged in a light absorbing or shielding material, a color difference of the preparation caused through irradiation with light of a total irradiation amount of 1.2 million lux·hr is Δ13 or less. As the light absorbing or shielding material, an aluminum or colored film may be used, and a package form can be an aluminum blister package.

Any shape can be employed as the shape of the tablet, and specifically, the shape can be a circle, an ellipse, a sphere, a bar or a doughnut shape. Besides, the tablet may be a layered tablet, a dry coated tablet or the like, and is preferably a single layered tablet produced by a simple production method. Furthermore, the tablet may be provided with a mark or characters for improving identification, or a score line for splitting.

EXAMPLES

Now, the present invention will be described in detail with reference to examples, comparative examples and reference examples, and it is noted that the present invention is not limited to these examples. A compound II can be produced by a method disclosed in International Publication No. WO2016/175224.

Example A Production Method for Compound I

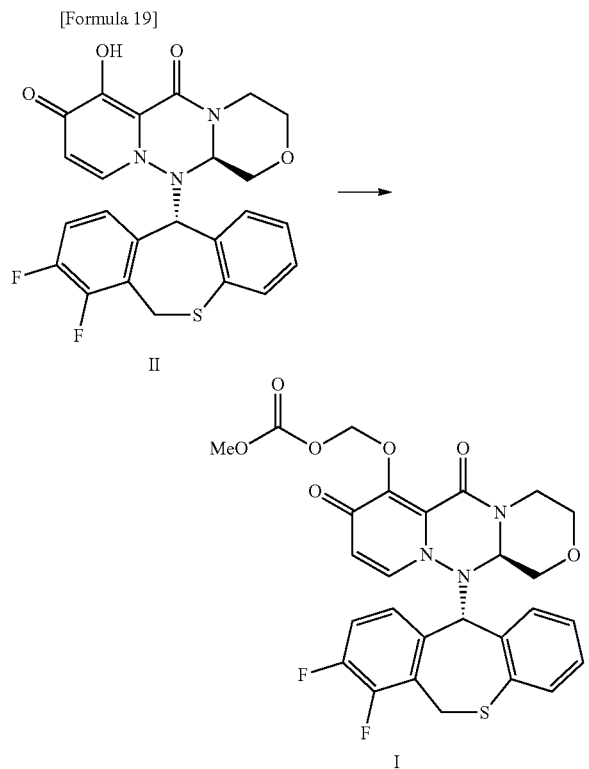

Potassium carbonate (1483.4 mg, 10.7 mmol), potassium iodide (549.5 mg, 3.3 mmol), tetrahydrofuran (33.1 g), N,N-dimethylacetamide (3.8 g) and water (80.3 mg) were added to the compound II (4.0 g, 8.3 mmol), followed by stirring. The resultant mixture was heated to 60° C., to which chloromethyl methyl carbonate (1758.9 mg, 14.2 mmol) was added. The resultant was stirred at 60° C. for 9 hours, and then cooled to 20° C. Acetic acid (822.0 mg), 2-propanol (3.1 g) and water (20.0 g) were added thereto, and the resultant was extracted twice with tetrahydrofuran (1.8 g, 8.9 g). The solvent was distilled off through vacuum concentration to a liquid weight of about 32 g. The resultant was heated to 45° C., 2-propanol (1.6 g) was added thereto, and the resultant was cooled to 20° C. A sodium acetate aqueous solution prepared from sodium acetate (339.0 mg) and water (46.0 g) was added thereto, followed by cooling to 5° C. After the resultant was stirred at 5° C. for 3 hours, a pale yellow precipitate was filtered off. The thus obtained solid was washed with a mixture of 2-propanol (4.7 g) and water (6.0 g), and the solid was then washed again with 2-propanol (6.3 g). To the thus obtained pale yellow solid, dimethyl sulfoxide (30.9 g) was added, followed by stirring. The resultant was heated to 60° C., to which a mixture of dimethyl sulfoxide (2.2 g) and water (4.8 g) was added. A mixture of dimethyl sulfoxide (19.9 g) and water (28.4 g) was further added thereto, followed by cooling to 20° C. After the resultant was stirred at 20° C. for 3 hours, a generated white precipitate was filtered off. The thus obtained solid was washed with a mixture of dimethyl sulfoxide (8.0 g) and water (4.8 g), and the solid was washed again with water (12.0 g). The thus obtained solid was dried to give a compound I (4.21 g) in the form of white crystal.

$^1$H-NMR (DMSO-D6) δ: 2.91-2.98 (1H, m), 3.24-3.31 (1H, m), 3.44 (1H, t, J=10.4 Hz), 3.69 (1H, dd, J=11.5, 2.8 Hz), 3.73 (3H, s), 4.00 (1H, dd, J=10.8, 2.9 Hz), 4.06 (1H, d, J=14.3 Hz), 4.40 (1H, d, J=11.8 Hz), 4.45 (1H, dd, J=9.9, 2.9 Hz), 5.42 (1H, dd, J=14.4, 1.8 Hz), 5.67 (1H, d, J=6.5 Hz), 5.72-5.75 (3H, m), 6.83-6.87 (1H, m), 7.01 (1H, d, J=6.9 Hz), 7.09 (1H, dd, J=8.0, 1.1 Hz), 7.14-7.18 (1H, m), 7.23 (1H, d, J=7.8 Hz), 7.37-7.44 (2H, m)

Powder X-ray Diffraction: 2θ (°): δ8.6±0.2°, 14.1±0.2°, 17.4±0.2°, 20.0±0.2°, 24.0±0.2°, 26.3±0.2°, 29.6±0.2° and 35.4±0.2°

(1) Study on Disintegrating Agent a. Compatibility Test

A test for compatibility between a compound represented by formula (I) and a disintegrating agent was performed to evaluate an amount of a related substance of a product stored over time. The compound represented by formula (I) and the disintegrating agent were mixed at 1:1 for wet preparation with water, and the resultant was stored at 40° C. and relative humidity of 75% for 2 weeks or 1 month to measure the amount of total related substances including the compound represented by formula (II). A method for measuring the total related substances is described below. As the disintegrating agent, low substituted hydroxypropyl cellulose (manufactured by Shin-Etsu Chemical Co., Ltd.), croscarmellose sodium (manufactured by FMC Bio Polymer), sodium carboxymethyl starch (manufactured by JRS Pharma) or crospovidone (manufactured by BASF) was used.

(Method for Measuring Total Related Substances)

The amount of the related substances was measured by liquid chromatography by employing the following method and conditions:

Detector: ultraviolet absorptiometer (measurement wavelength: 260 nm)

Column: XBridge C18, 3.5 μm, 3.0×150 mm

Column temperature: constant temperature around 35° C.

Mobile Phase A: 0.1% trifluoroacetic acid/0.2 mM EDTA solution, Mobile Phase B: acetonitrile Delivery of mobile phase: controlled for a concentration gradient with a mixing ratio between the mobile phase A and the mobile phase B changed as shown in Table 1

TABLE 1

| Time after Injection (min) | Mobile Phase A (vol %) | Mobile Phase B (vol %) |
|---|---|---|
| 0-5 | 70 | 30 |
| 5-40 | 70 → 20 | 30 → 80 |
| 40-40.1 | 20 → 70 | 80 → 30 |

Flow rate: about 0.6 mL/min (retention time of compound represented by formula (I): 16 minutes)

Injection amount: 5 μL

Sample cooler temperature: about 5° C.

Washing solution for autoinjector: acetonitrile/methanol mixture (1:3)

Range of area measurement: 50 minutes after injection of sample solution

Equation for calculating amount of total related substances:

$$\text{Total amount of total related substances (\%)} = \frac{\sum A_{Ti}}{\sum A_T} \times 100$$

$A_{Ti}$: peak area of each related substance in sample solution $\sum A_T$: Sum of peak areas of sample solution (excluding blank and system peaks)

$\sum A_{Ti}$: Sum of peak areas of each related substances of sample solution (Results)

The thus obtained amount of total related substances is shown in Table 2. As a result, the amount of the total related substances tended to be lower in using low substituted hydroxypropyl cellulose and croscarmellose sodium than in using sodium carboxymethyl starch and crospovidone.

TABLE 2

| Disintegrating Agent | Low Substituted Hydroxypropyl Cellulose | Croscarmellose Sodium | Sodium Carboxymethyl Starch | Crospovidone |
|---|---|---|---|---|
| Amount of Total Related Substances (%) 2 weeks after | 0.72 | 0.76 | 0.94 | 0.93 |
| Amount of Total Related Substances (%) 1 month after | 0.72 | 0.75 | 1.10 | 0.99 | b. Dissolution Property of Compound Represented by Formula (I)

(Method for Producing Uncoated Tablet)

The low substituted hydroxypropyl cellulose and croscarmellose sodium, which were found to generate a small amount of total related substances, were selected as the disintegrating agent to produce a tablet containing these disintegrating agents, and the tablet was subjected to a dissolution test.

Table 3 shows formulation, per tablet of the present preparation, of a light stabilizing substance and a polymer in an uncoated tablet obtained before coating. The compound represented by formula (I), lactose hydrate (manufactured by DMV-Fonterra Excipients) and the disintegrating agents were sieved through a 30-mesh sieve, and the resultant was granulated using a high-speed mixer (manufactured by Fukae Kogyo Co., Ltd., LFS-GS-2J). In the granulation, an aqueous solution of polyvinyl pyrrolidone (manufactured by BASF) was used as a binder. It is noted that a moisture in the granulation was adjusted to about 20% or 40%.

TABLE 3

|  | Uncoated Tablet 1-1 | Uncoated Tablet 1-2 | Uncoated Tablet 2-1 | Uncoated Tablet 2-2 |
|---|---|---|---|---|
| Compound represented by Formula (I) | 20.0 | 20.0 | 20.0 | 20.0 |
| Lactose Hydrate | 72.4 | 72.4 | 72.4 | 72.4 |
| Low Substituted Hydroxypropyl Cellulose | 11.0 | 11.0 | — | — |
| Croscarmellose Sodium | — | — | 11.0 | 11.0 |
| Polyvinyl Pyrrolidone | 5.5 | 5.5 | 5.5 | 5.5 |
| Crystalline Cellulose | 10.0 | 10.0 | 10.0 | 10.0 |
| Sodium Stearyl Fumarate | 1.1 | 1.1 | 1.1 | 1.1 |
| Sum in Uncoated Tablet (mg) | 120.0 | 120.0 | 120.0 | 120.0 |
| Moisture in Granulation (% (w/w)) | 21.3 | 41.3 | 21.3 | 41.4 |

Granulation conditions and a method of the dissolution test were as follow:

(Granulation Conditions)

Granulator: LFS-GS-2J high-speed mixer

Rotational Speed of Agitator: 333 min$^{-1}$

Rotational Speed of Chopper: 2500 min$^{-1}$

Acceleration in Solution Injection: 20 g/min

A granule obtained through the granulation, drying and size selection, crystalline cellulose and stearyl sodium fumarate (manufactured by JRS Pharma) used as a lubricant were mixed, and the resultant was tableted at 5 kN using a static compressor to produce a tablet.

(Method of Dissolution Test)

The dissolution test was performed in accordance with the second method of Dissolution Test described in the Japanese Pharmacopoeia 16th edition (dissolution test second fluid containing surface active agent, paddle method, rotational speed of paddle: 50 rpm, result: average of two tablets).

(Results of Experiment)

Figure 2:
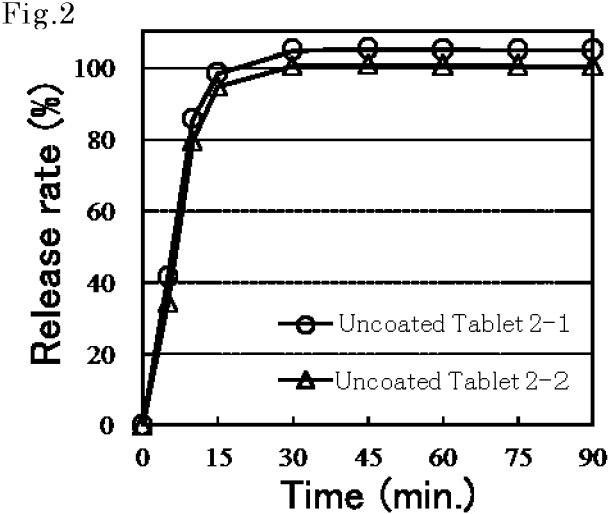
FIG. 2 illustrates dissolution behavior of a tablet using croscarmellose sodium as a disintegrating agent.

Results of the dissolution test of uncoated tablets 1-1 and 1-2 are illustrated in FIG. 1, and results of the dissolution test of uncoated tablets 2-1 and 2-2 are shown in FIG. 2. As a result, when low substituted hydroxypropyl cellulose was used as the disintegrating agent, dissolution behavior of the preparation of the uncoated table 1-2 using a moisture of about 40% in granulation was slower than that of the preparation of the uncoated tablet 1-1 using the moisture of about 20% in granulation. On the other hand, when croscarmellose sodium was used as the disintegrating agent, the dissolution behavior was substantially the same in the preparation of the uncoated tablet 2-1 using the moisture of about 20% in granulation and the preparation of the coated tablet 2-2 using the moisture of about 40% in granulation. Accordingly, it was regarded that croscarmellose sodium is most suitably used as the disintegrating agent because it generates a small amount of total related substances in the compatibility test, and in addition, it substantially does not change the dissolution property even when the moisture used in granulation is changed.

(2) Selection of Light Stabilizing Substance and Polymer a. Influence of Light Stabilizing Substance In order to check the influence of the light stabilizing substance, an uncoated tablet was coated with the light stabilizing substance and the polymer to measure the amount of related substances generated in the preparation and the color difference. Formulations of preparations coated with the light stabilizing substance and the polymer are shown in Table 4. Titanium oxide and talc were used as the light stabilizing substances, polyvinyl alcohol was used as the polymer, and macrogol 4000 was used as the plasticizer. As the amount of a related substance, the amount of the compound represented by formula (II) and the amount of total related substances were measured. Besides, a color difference of each preparation was measured as a color difference of the preparation obtained after exposure to prescribed light.

TABLE 4

| Material | Example 1 | Example 2 | Example 3 | Comparative Example 1 |
|---|---|---|---|---|
| Compound represented by Formula (I) | 20.0 | 20.0 | 20.0 | 20.0 |
| Lactose Hydrate | 77.9 | 77.9 | 77.9 | 77.9 |
| Croscarmellose Sodium | 5.5 | 5.5 | 5.5 | 5.5 |
| Polyvinyl Pyrrolidone | 5.5 | 5.5 | 5.5 | 5.5 |
| Crystalline Cellulose | 10.0 | 10.0 | 10.0 | 10.0 |
| Sodium Stearyl Fumarate | 1.1 | 1.1 | 1.1 | 1.1 |
| Sum in Uncoated Tablet (mg) | 120.00 | 120.00 | 120.00 | 120.00 |
| Polyvinyl Alcohol | 1.24 | 1.84 | 2.56 | — |
| Titanium Oxide | 0.78 | 1.15 | 1.60 | — |
| Talc | 0.46 | 0.68 | 0.95 | — |
| Macrogol 4000 | 0.63 | 0.93 | 1.29 | — |
| Sum in Coated Tablet (mg) | 123.11 | 124.60 | 126.40 | 120.00 |

A method for producing a coated preparation, coating conditions, a method for measuring the compound represented by formula (II), and a method for measuring the color difference of the preparation were as follows:

(Method for Producing Coated Preparation)

Table 4 shows an uncoated tablet corresponding to one tablet of the present preparation and the amounts of the light stabilizing substance (titanium oxide and talc) and the polymer (polyvinyl alcohol) used for coating the uncoated tablet. The surface of each uncoated tablet was coated with the light stabilizing substances and the polymer. As a machine used for the coating, High Coater Labo (manufactured by Freund Corp.) was used. The conditions for performing the coating are as follows:

(Coating Conditions)
Charged amount: about 0.5 kg
Coating machine: Labo Coater HC-LABO (Freund Corp.)
Temperature of supplied air: 60° C. (preset temperature)
Flow rate of supplied air: 1.0 m$^3$/min
Nozzle diameter: 1.0 mm
Nozzle cap diameter: 1.3 mm
Flow rate of sprayed air: about 40 NL/min
Speed of coating solution: about 2 g/min
Rotational speed of pan: 25 to 32 min$^{-1}$ (Method for Measuring Compound Represented by Formula (II))

The amount of the compound represented by formula (II) was measured by the liquid chromatography by employing the following method and conditions:
Detector: ultraviolet absorptiometer (measurement wavelength: 260 nm)
Column: XBridge C18, 3.5 μm, 3.0×150 mm
Column temperature: constant temperature around 35° C.
Mobile Phase A: 0.1% trifluoroacetic acid/0.2 mM EDTA solution, Mobile Phase B: acetonitrile
Delivery of mobile phase: controlled for a concentration gradient with a mixing ratio between the mobile phase A and the mobile phase B changed as shown in Table 5

TABLE 5

| Time after Injection (min) | Mobile Phase A (vol %) | Mobile Phase B (vol %) |
|---|---|---|
| 0-5 | 70 | 30 |
| 5-40 | 70 → 20 | 30 → 80 |
| 40-40.1 | 20 → 70 | 80 → 30 |

Flow rate: about 0.6 mL/min
Injection amount: 5 μL
Sample cooler temperature: about 5° C.
Washing solution for autoinjector: acetonitrile/methanol mixture (1:3)
Range of area measurement: 50 minutes after injection of sample solution
Equation for calculating amount of compound represented by formula (II):

$$\text{Amount of compound represented by formula (II) (\%)} = \frac{A_{TII}}{\sum A_T} \times 100$$

$A_{TII}$: peak area of compound represented by formula (II) in sample solution $\sum A_T$: Sum of peak areas of sample solution (excluding blank and system peaks)

(Method for Measuring Color Difference)

A spectrocolorimeter (having a lens diameter of 4 mm) was used to measure color tones (ΔE) of one to three sample tablets of each tablet based on initial one in accordance with the following calculation formula, and an average value thereof was calculated in according with the following expression. It is noted that L denotes brightness, a denotes chromaticity (+: redness, −: greenness), and b denotes chromaticity (+: yellowness, −: blueness). Besides, Table 6 shows criteria for evaluating appearance using the colorimeter.

$$\Delta E = \{(\Delta L)^2 + (\Delta a)^2 + (\Delta b)^2\}^{1/2}$$

TABLE 6

| ΔE | Criteria for Appearance |
|---|---|
| 0-less than 0.5 | Faintly |
| 0.5-less than 1.5 | Slightly |

TABLE 6-continued

| ΔE | Criteria for Appearance |
|---|---|
| 1.5-less than 3.0 | Recognizably |
| 3.0-less than 6.0 | Conspicuously |
| 6.0-less than 12.0 | Considerably |
| 12.0 or more | Greatly |

(Experiment Results)

Table 7 shows the amounts (%) of the compound represented by formula (II) obtained with a container uncapped at 40° C. and relative humidity of 75% at an initial time, 2 weeks after and 1 month after, and Table 8 shows the amounts (%) of total related substances. Besides, Table 9 shows the color difference (ΔE) of each preparation obtained after irradiation with light of 1.2 million lux·hr.

As a result, at 40° C. and relative humidity of 75% with the container uncapped, the amounts of the compound represented by formula (II) and the amounts of total related substances were minimally changed in the preparations of Examples 1 to 3 and the preparation of Comparative Example 1 from the initial time up to 1 month after starting the experiment. On the other hand, the color difference of the preparation was 12 or more, and was larger in the preparation of Comparative Example 1 not coated with the light stabilizing substance as compared with the preparations of Examples 1 to 3 coated with the light stabilizing substance, and according to the criteria for evaluating appearance shown in Table 6, it was revealed that the color difference of the preparation was changed "greatly".

TABLE 7

| Amount of Compound represented by Formula (II) (%) | Example 1 | Example 2 | Example 3 | Comparative Example 1 |
|---|---|---|---|---|
| Initial | 0.09 | 0.08 | 0.10 | 0.10 |
| 2 Weeks after | 0.13 | 0.13 | 0.13 | 0.14 |
| 1 Month after | 0.15 | 0.17 | 0.14 | 0.16 |

TABLE 8

| Amount of Total Related Substances %) | Example 1 | Example 2 | Example 3 | Comparative Example 1 |
|---|---|---|---|---|
| Initial | 0.50 | 0.57 | 0.55 | 0.61 |
| 2 Weeks after | 0.55 | 0.60 | 0.62 | 0.62 |
| 1 Month after | 0.62 | 0.62 | 0.72 | 0.61 |

TABLE 9

| Color Difference of Preparation (ΔE) | Example 1 | Example 2 | Example 3 | Comparative Example 1 |
|---|---|---|---|---|
| 1.2 Million lux · hr (exposure) | 0.76 | 0.72 | 1.05 | 14.44 | c. Optimization of Light Stabilizing Substance and Polymer

In order to optimize the light stabilizing substance and the polymer, an uncoated tablet was coated with the light stabilizing substance and the polymer to measure the amount of related substances in a preparation and the color difference of the preparation. Formulations of preparations coated with the light stabilizing substance and the polymer are shown in Table 10. Titanium oxide and talc were used as the light stabilizing substance, polyvinyl alcohol, hydroxypropyl cellulose or hypromellose was used as the polymer, and macrogol 4000 was used as the plasticizer.

TABLE 10

| Material | Example 4 | Example 5 | Example 6 |
|---|---|---|---|
| Compound represented by Formula (I) | 20.0 | 20.0 | 20.0 |
| Lactose Hydrate | 77.9 | 77.9 | 77.9 |
| Croscarmellose Sodium | 5.5 | 5.5 | 5.5 |
| Polyvinyl Pyrrolidone | 5.5 | 5.5 | 5.5 |
| Crystalline Cellulose | 10.0 | 10.0 | 10.0 |
| Sodium Stearyl Fumarate | 1.1 | 1.1 | 1.1 |
| Sum in Uncoated Tablet (mg) | 120.00 | 120.00 | 120.00 |
| Polyvinyl Alcohol | 1.92 | — | — |
| Hydroxypropyl Cellulose | — | 2.16 | — |
| Hypromellose | — | — | 2.88 |
| Titanium Oxide | 1.20 | 1.20 | 0.96 |
| Talc | 0.71 | 1.44 | 0.96 |
| Macrogol 4000 | 0.97 | — | — |
| Sum in Coated Tablet (mg) | 124.80 | 124.80 | 124.80 |

(Experiment Results)

Table 11 shows the amounts (%) of the compound represented by formula (II) obtained with a container uncapped at 40° C. and relative humidity of 75% at an initial time and 2 weeks after, and Table 12 shows the amounts (%) of total related substances. Besides, Table 13 shows the color difference (ΔE) of each preparation obtained after irradiation with light of 1.2 million lux·hr.

As a result, at 40° C. and relative humidity of 75% with the container uncapped, the amounts of the compound represented by formula (II) and the amounts of total related substances were minimally changed in the preparations of Examples 4 to 6 from the initial time up to 2 weeks after starting the experiment. In particular, in the preparation of Example 6 using titanium oxide and talc as the light stabilizing substance and hypromellose as the polymer, the amount of the total related substances was minimally increased. In the preparations coated with the light stabilizing substance of Examples 4 to 6, the color difference was minimally changed, and the color difference was changed to an extent as evaluated as "faintly" or "slightly" according to the criteria for evaluating appearance shown in Table 6.

TABLE 11

| Amount of Compound represented by Formula (II) (%) | Example 4 | Example 5 | Example 6 |
|---|---|---|---|
| Initial | 0.08 | 0.09 | 0.11 |
| 2 Weeks after | 0.13 | 0.15 | 0.13 |

TABLE 12

| Amount of Total Related Substances (%) | Example 4 | Example 5 | Example 6 |
|---|---|---|---|
| Initial | 0.57 | 0.55 | 0.61 |
| 2 Weeks after | 0.60 | 0.64 | 0.59 |

TABLE 13

| Color Difference of Preparation (ΔE) | Example 4 | Example 5 | Example 6 |
|---|---|---|---|
| 1.2 Million lux · hr (exposure) | 0.72 | 0.47 | 0.93 |

Clinical Test

The efficacy and safety of a single oral administration of an investigational drug (active ingredient: Compound represented by Formula (I) (Hereinafter, this compound is sometimes referred to as the "Compound II-6"): 10 mg, 20 mg, 40 mg) to patients infected by influenza virus were evaluated by a randomized, placebo-controlled, double-blind comparative study. As for the primary endpoint, subjects made evaluations by themselves on a 4-point scale [0:

Dosage and Administration Method

Eligible subjects were randomly allocated to a Compound II-6 10 mg group, 20 mg group, 40 mg group, and placebo group in a ratio of 1:1:1:1. Subjects received a single oral administration of total 3 tables of Compound II-6 tablets and/or placebo tablets in a combination indicated in the following table on Day 1.

Investigational Drug for Each Administered Group

TABLE 14

| Treatment Groups | Compound II-6 10 mg tablet | Compound II-6 20 mg tablet | Placebo tablet Matching Compound II-6 10 mg tablet | Placebo tablet Matcing Compound II-6 20 mg tablet |
|---|---|---|---|---|
| Compound II-6 10 mg tablet | 1 tablet | — | — | 2 tablets |
| Compound II-6 20 mg tablet | — | 1 tablet | 1 tablet | 1 tablet |
| Compound II-6 40 mg tablet | — | 2 tablets | 1 tablet | — |
| Placebo | — | — | 1 tablet | 2 tablets | none, 1: mild, 2: moderate, 3: severe] concerning the time to alleviation of influenza symptoms (the time from the beginning of administration of the investigational drug until 7 influenza symptoms ("cough", "sore throat", "headache", "nasal congestion", "feverishness or chills", "muscular or joint pain", and "fatigue") were alleviated) to evaluate the efficacy of the investigational drug over the placebo.
Patients who satisfied all of the following criteria were selected as subjects.
(a) Male or female patients at 20 years old or older and younger than 65 years old
(b) Patients satisfying all of the following criteria and diagnosed with influenza virus infectious disease
 Positive in influenza rapid diagnosis [Rapid antigen test (RAT)] based on a nasal or throat swab
 Body temperature (axillary temperature) of 38.0° C. or higher
 Having one or more moderate or severer symptoms among the following systemic symptoms and respiratory symptoms due to influenza virus infectious disease
  Systemic symptoms (headache, feverishness or chills, muscular or joint pain, fatigue)
  Respiratory symptoms (cough, sore throat, nasal congestion)
(C) Patients within 48 hours from onset (at registration)
The definition of onset is any of the following.
 When the body temperature increased for the first time (at least an increase of 1° C. from normal temperature)
 When any one or more of the systemic symptoms and respiratory symptoms were developed
Method for Administering Investigational Drug
(i) Test Drug
10 mg Tablet of Compound II-6: White to pale yellowish white, circular, film-coated tablet (present preparation) containing 10 mg of Compound II-6
20 mg Tablet of Compound II-6: White to pale yellowish white, elliptical, film-coated tablet (present preparation) containing 20 mg of Compound II-6
(ii) Placebo or Control Drug
Placebo for 10 mg tablet of Compound II-6: Tablet undistinguishable from 10 mg tablet of Compound II-6
Placebo for 20 mg tablet of Compound II-6: Tablet undistinguishable from 20 mg tablet of Compound II-6

Main Efficacy Endpoint

The main efficacy endpoint is the time to alleviation of influenza symptoms (the time to alleviation of influenza symptoms).

It is the time from the beginning of administration until alleviation of influenza symptoms. Alleviation of influenza symptoms refers to when all 7 influenza symptoms (cough, sore throat, headache, nasal congestion, feverishness or chills, muscular or joint pain, fatigue) become "0: none" or "1: mild" in the patient diary that the subject keeps, and this condition continues at least 21.5 hours (24 hours—10%).
Secondary Efficacy Endpoint The secondary efficacy endpoint is as follows.
(1) Time to Alleviation of Each Influenza Symptom It is the time from the beginning of administration until alleviation of each influenza symptom. Alleviation of a symptom refers to when the target item becomes "0: none" or "1: mild", and this condition continues at least 21.5 hours (24 hours—10%).
Analysis of Primary Endpoint As for the time to alleviation of influenza symptoms, which is the primary endpoint, the primary analysis and the secondary analysis are described. In addition to the ITTI group, the primary analysis was also performed on the PPS group for sensitivity analysis. Other analyses were performed only on the ITTI group.
(1) Primary Analysis The hazard ratio, 95% confidence interval, and P value of each administered group relative to the placebo group were calculated by a Cox proportional hazard model using the time to alleviation of influenza symptoms as a response, the administered groups as fixed effects, and the current smoking habit and the total score of 7 influenza symptoms at baseline before administration, which are allocation factors, as covariates. In order to prevent an increase of the probability of type I error due to performing the test multiple times, the P value was adjusted by the Hommel's method.
(2) Secondary Analysis The placebo group and each investigational drug administered group were compared by stratified generalized Wilcoxon test using the time to alleviation of influenza symptoms as a response, the administered groups as explanatory variables, and the category (11 points or less, 12 points or more) of the total score of 7 influenza symptoms before administration and the smoking habit, which are allocation factors, as stratification factors.

Also, a Kaplan-Meier survival curve was drawn for each group to calculate the median time to alleviation of influenza symptoms and the 95% confidence interval thereof. The Greenwood's method was used for calculating the confidence interval.

Analysis of Secondary Endpoint
(1) Time Until Each Alleviation of Influenza Symptom The same analysis as in the primary endpoint was performed, with the time until each alleviation of influenza symptom being regarded as a response. At this time, cases where the symptom before administration was "0: none" or "1: mild" were excluded from the analysis target.

(1) Results of Primary Endpoint (Time to Alleviation of Influenza Symptoms)

Out of 400 randomly selected patients, 389 patients (98 patients (98%) in the 10 mg administered group, 95 patients (95%) in the 20 mg administered group, 99 patients (99%) in the 40 mg administered group, and 97 patients (97%) in the placebo group) completed the test. As for the primary endpoint, the ITTI Population (cases where an investigational drug was administered, and influenza virus infection was confirmed) consisted of 400 patients.

The per protocol set cases consisted of 368 patients (89 patients (89%) in the 10 mg administered group, 92 patients (92%) in the 20 mg administered group, 96 patients (96%) in the 40 mg administered group, and 91 patients (91%) in the placebo group). As for the ITTI Population of each group, it was found from the rapid antigen detection test that 75% to 79% of the patients were infected by influenza A virus, and 21% to 25% of the patients were infected by influenza B virus.

Analysis results are shown in the following tables.

TABLE 15

|  | Testdrug 10 mg administered group | Testdrug 20 mg administered group | Testdrug 40 mg administered group | Placebo administered group |
|---|---|---|---|---|
| N (human) | 100 | 100 | 100 | 100 |
| Median value (hour) | 54.2 | 51 | 49.5 | 77.7 |
| 95% Confdence interval (hour) | 47.7, 66.8 | 44.5, 62.4 | 44.5, 64.4 | 67.6, 88.7 |
| Difference from placebo (hour) Generalized Wilson test | −23.4 | −26.6 | −28.2 | — |
| P value Cox proportional hazard model relative to placebo | 0.0085 | 0.0182 | 0.0046 | — |
| Hazard ratio | 0.758 | 0.81 | 0.817 | — |
| 95% Confdence interval | 0.571, 1.007 | 0.608, 1.078 | 0.614, 1.087 | — |
| P value | 0.0561 | 0.1488 | 0.165 | — |

The primary endpoint of this test, i.e., the median time until the symptoms were alleviated, was 54.2 hours in the 10 mg administered group (95% CI: 47.7, 66.8), 51.0 hours in the 20 mg administered group (95% CI: 47.7, 66.8), 49.5 hours in the 40 mg administered group (95% CI: 44.5, 64.4), and 77.7 hours in the placebo group (95% CI: 67.6, 88.7).

(2) Time Until Each of the Seven Symptoms is Alleviated

The following tables show the results of analyzing the time until each of the 7 influenza symptoms ("cough", "sore throat", "headache", "nasal congestion", "feverishness or chills", "muscular or joint pain", "fatigue") is alleviated.

(i) Time Until "Nasal Congestion" Symptom is Alleviated

TABLE 16

|  | Testdrug 10 mg administered group | Testdrug 20 mg administered group | Testdrug 40 mg administered group | Placebo administered group |
|---|---|---|---|---|
| N (human) | 49 | 38 | 45 | 47 |
| Median value (95% CI) (hour) | 25.2 (19.0, 47.2) | 21.6 (13.4, 30.5) | 21.9 (16.0, 28.7) | 42.8 (22.9, 68.3) |
| Difference from placebo (hour) | −17.6 | −21.3 | −21 | — |
| P value (G. Wilcoxon test) [a] | 0.043 | 0.0516 | 0.0003 | — |

TABLE 16-continued

|  | Testdrug 10 mg administered group | Testdrug 20 mg administered group | Testdrug 40 mg administered group | Placebo administered group |
|---|---|---|---|---|
| Hazard ratio | 0.742 | 0.59 | 0.564 | — |
| 95% CI [b] | (0.494, 1.114) | (0.379, 0.920) | (0.369, 0.862) | — |
| P value (Cox model) [b] | 0.15 | 0.0199 | 0.0081 | — |

(ii) Time Until "Muscular or Joint Pain" Symptom is Alleviated

TABLE 17

|  | Testdrug 10 mg administered group | Testdrug 20 mg administered group | Testdrug 40 mg administered group | Placebo administered group |
|---|---|---|---|---|
| N (human) | 73 | 7 | 71 | 71 |
| Median value | 31.2 | 29.9 | 25.4 | 41.9 |
| (95% CI) (hour) | (24.9, 39.9) | (22.8, 37.0) | (20.5, 28.9) | (28.7, 48.6) |
| Difference from placebo (hour) | −10.7 | −12 | −16.4 | — |
| P value (G. Wilcoxon test) [a] | 0.2153 | 0.0346 | 0.0048 | — |
| Hazard ratio | 0.77 | 0.687 | 0.657 | — |
| (95% CI) [b] | (0.553, 1.072) | (0.494, 0.955) | (0.469, 0.920) | — |
| P value (Cox model) [b] | 0.1217 | 0.0255 | 0.0145 | — |

(iii) Time Until "Fatigue" Symptom is Alleviated

TABLE 18

|  | Testdrug 10 mg administered group | Testdrug 20 mg administered group | Testdrug 40 mg administered group | Placebo administered group |
|---|---|---|---|---|
| N (human) | 82 | 82 | 7 | 79 |
| Median value | 32 | 31.3 | 31.1 | 42.7 |
| (95% CI) (hour) | (29.2, 39.9) | (26.7, 42.4) | (24.6, 38.6) | (30.3, 53.2) |
| Difference from placebo (hour) | −10.7 | −11.5 | −11.7 | — |
| P value (G. Wilcoxon test) [a] | 0.1221 | 0.0594 | 0.0224 | — |
| Hazard ratio | 0.783 | 0.876 | 0.724 | — |
| (95% CI) [b] | (0.574, 1.069) | (0.637, 1.203) | (0.527, 0.995) | — |
| P value (Cox model) [b] | 0.1236 | 0.412 | 0.0463 | — |

(iv) Time Until "Feverishness or Chills" Symptom is Alleviated

TABLE 19

|  | Testdrug 10 mg administered group | Testdrug 20 mg administered group | Testdrug 40 mg administered group | Placebo administered group |
|---|---|---|---|---|
| N (human) | 9 | 93 | 94 | 95 |
| Median value | 24.7 | 29.4 | 23 | 28.8 |
| (95% CI) (hour) | (21.3, 28.4) | (22.0, 34.8) | (19.8, 28.6) | (21.1, 33.4) |
| Difference from placebo (hour) | −4.1 | 0.6 | −5.8 | — |
| P value (G. Wilcoxon test) [a] | 0.0602 | 0.3774 | 0.0258 | — |
| Hazard ratio | 0.635 | 0.848 | 0.71 | — |
| (95% CI) [b] | (0.475, 0.850) | (0.634, 1.133) | (0.529, 0.951) | — |
| P value (Cox model) [b] | 0.0023 | 0.2642 | 0.0216 | — |

(v) Time Until "Headache" Symptom is Alleviated

TABLE 20

|  | Testdrug 10 mg administered group | Testdrug 20 mg administered group | Testdrug 40 mg administered group | Placebo administered group |
|---|---|---|---|---|
| N (human) | 61 | 58 | 54 | 5 |
| Median value (95% CI) (hour) | 42.2 (29.8, 47.3) | 37 (28.5, 43.5) | 37.9 (28.6, 44.5) | 43.7 (29.7, 53.6) |
| Difference from placebo (hour) | −1.5 | −6.7 | −5.8 | — |
| P value (G. Wilcoxon test) [a] | 0.6846 | 0.7741 | 0.0904 | — |
| Hazard ratio (95% CI) [b] | 0.803 (0.557, 1.157) | 0.936 (0.635, 1.381) | 0.655 (0.447, 0.961) | — |
| P value (Cox model) [b] | 0.2388 | 0.7404 | 0.0304 | — |

(vi) Time Until "Cough" Symptom is Alleviated

TABLE 21

|  | Testdrug 10 mg administered group | Testdrug 20 mg administered group | Testdrug 40 mg administered group | Placebo administered group |
|---|---|---|---|---|
| N (hum an) | 74 | 74 | 78 | 75 |
| Median value (95% CI) (hour) | 31.1 (21.3, 41.5) | 29.8 (21.9, 32.9) | 24.6 (16.1, 29.4) | 31.2 (20.9, 51.4) |
| Difference from placebo (hour) | −0.1 | −1.4 | −6.6 | — |
| P value (G. Wilcoxon test) [a] | 0.6643 | 0.8536 | 0.1551 | — |
| Hazard ratio (95% CI) [b] | 0.941 (0.675, 1.312) | 0.883 (0.636, 1.226) | 0.865 (0.626, 1.196) | — |
| P value (Cox model) [b] | 0.7188 | 0.4569 | 0.3796 | — |

(vii) Time Until "Sore Throat" Symptom is Alleviated

TABLE 22

|  | Testdrug 10 mg administered group | Testdrug 20 mg administered group | Testdrug 40 mg administered group | Placebo administered group |
|---|---|---|---|---|
| N (human) | 56 | 64 | 55 | 46 |
| Median value (95% CI) (hour) | 35.3 (21.2, 49.8) | 27.8 (19.9, 32.1) | 31.9 (17.3, 43.0) | 26.3 (16.5, 45.2) |
| Difference from placebo (hour) | 9.1 | 1.5 | 5.6 | — |
| P value (G. Wilcoxon test) [a] | 0.2905 | 0.6293 | 0.993 | — |
| Hazard rato (95% CI) [b] | 1.312 (0.882, 1.951) | 1.05 (0.713, 1.547) | 1.092 (0.738, 1.617) | — |
| P value (Cox model) [b] | 0.18 | 0.8047 | 0.6602 | — |

Subset of patients whose score of symptoms at baseline was "moderate" or "severe" CI: Confidence interval
a Stratified generalized Wilson test relative to placebo. Stratification factors: Smoking habit, and composite symptom scores at baseline.
b Cox proportional hazard model relative to placebo. Covariates: Smoking habit, and composite symptom scores at baseline.

An analysis using a Cox proportional hazard model revealed that the 40 mg administered group in comparison to the placebo group showed a significant decrease in time until the following 5 symptoms: "nasal congestion", "muscular or joint pain", "fatigue", "feverishness or chills", and "headache" were alleviated. For example, as for 2 symptoms, i.e., "nasal congestion" and "muscular or joint pain", the median times until these symptoms were improved were 21.0 hours and 16.4 hours, respectively, and they were shorter in the 40 mg administered group than the placebo group.

Statistically significant differences were observed also in the 10 mg administered group and the 20 mg administered group with respect to the following symptoms: "muscular or joint pain", "nasal congestion", and "feverishness or chills".
Clinical Test (Ph3: Adults and Adolescents)

The efficacy and safety of a single oral administration of an investigational drug (active ingredient (Compound II-6): 40 mg, 80 mg) to patients infected by influenza virus were evaluated by a randomized, double-blind comparative study in comparison to 75 mg Oseltamivir administered twice per day for 5 days or a placebo. As for the primary endpoint, subjects made evaluations by themselves on a 4-point scale

[0: none, 1: mild, 2: moderate, 3: severe] concerning the time to alleviation of influenza symptoms (the time from the beginning of administration of the investigational drug until 7 influenza symptoms ("cough", "sore throat", "headache", "nasal congestion", "feverishness or chills", "muscular or joint pain", and "fatigue") were alleviated) to evaluate the efficacy of the investigational drug over the placebo.

Moreover, as for the secondary efficacy endpoint, the efficacy and the side effects of the investigational drug were evaluated according to the influenza virus titer using a nasal or throat swab.

Patients who satisfied all of the following criteria were selected as subjects.

(a) Male or female patients at 12 years old or older and younger than 65 years old (b) Patients satisfying all of the following criteria and diagnosed with influenza virus infectious disease Body temperature (axillary temperature) of 38.0° C. or higher Having one or more moderate or severer symptoms among the following systemic symptoms and respiratory symptoms due to influenza virus infectious disease Systemic symptoms (headache, feverishness or chills, muscular or joint pain, fatigue)

Respiratory symptoms (cough, sore throat, nasal congestion)

(c) Patients within 48 hours from onset (at registration)

The definition of onset is any of the following.

When the body temperature increased for the first time (at least an increase of 1° C. from normal temperature)

When any one or more of the systemic symptoms and respiratory symptoms were developed Method for Administering Investigational Drug (i) Test Drug 20 mg Tablet of Compound II-6

(ii) Placebo or Control Drug

Placebo for 20 mg tablet of Compound II-6

75 mg Capsule of Oseltamivir

Placebo for 75 mg capsule of Oseltamivir: Capsule undistinguishable from 75 mg capsule of Oseltamivir Dosage and Administration Method Eligible patients at 20 to 64 years old were randomly allocated to a group receiving a single administration of Compound II-6 (40 or 80 mg depending on the body weight), a group receiving 75 mg Oseltamivir twice a day for 5 days, and a placebo group in a ratio of 2:2:1.

Eligible patients at 12 to 19 years old were randomly allocated to a group receiving a single administration of Compound II-6 (40 or 80 mg depending on the body weight) and a placebo administered group in a ratio of 2:1.

The dosage of Compound II-6 was 40 mg for subjects weighing less than 80 kg, and 80 mg for subjects weighing 80 kg or more.

Investigational Drug for Each Administered Group

[Compound II-6 Group]

Day 1:

20 mg Tablets of Compound II-6 were administered orally (2 tablets or 4 tablets depending on the body weight). Placebo capsules for Oseltamivir were administered orally twice a day (morning, evening), one capsule per administration.

Day 2 to Day 5:

Placebo capsules for Oseltamivir were administered orally twice a day (morning, evening), one capsule per administration.

[Oseltamivir Group]

Day 1:

Placebo tablets for Compound II-6 were administered orally (2 tablets or 4 tablets depending on the body weight). 75 mg Capsules of Oseltamivir were administered orally twice a day (morning, evening), one capsule per administration.

Day 2 to Day 5:

75 mg Capsules of Oseltamivir were administered orally twice a day (morning, evening), one capsule per administration.

[Placebo Group]

Day 1:

Placebo tablets for Compound II-6 were administered orally (2 tablets or 4 tablets depending on the body weight). Placebo capsules for Oseltamivir were administered orally twice a day (morning, evening), one capsule per administration.

Day 2 to Day 5:

Placebo capsules for Oseltamivir were administered orally twice a day (morning, evening), one capsule per administration.

"Day 1" indicates the first day of administration, and "Day 2 to Day 5" indicates the second day to the fifth day as counted from the first day of administration.

Main Efficacy Endpoint

The main efficacy endpoint is the time to alleviation of influenza symptoms (the time to alleviation of influenza symptoms).

It is the time from the beginning of administration until alleviation of influenza symptoms. Alleviation of influenza symptoms refers to when all 7 influenza symptoms (cough, sore throat, headache, nasal congestion, feverishness or chills, muscular or joint pain, fatigue) become "0: none" or "1: mild" in the patient diary that the subject keeps, and this condition continues at least 21.5 hours (24 hours—10%).

Secondary Efficacy Endpoint

The secondary efficacy endpoint is as follows.

(1) Proportion of patients having a positive influenza virus titer at each point (2) Amount of change in virus titer from baseline at each point (3) Time to termination of viral shedding based on virus titer (4) Incidence of side effects The virus titer was measured in the following manner.

(1) MDCK-SIAT1 cells seeded in a flat-bottom 96-well microplate were cultured in a 5% $CO_2$ incubator at 37±1° C. for 1 day.

(2) A standard strain (influenza virus AH3N2, A/Victoria/361/2011, storage condition: −80° C., origin: National Institute of Infectious Diseases), a sample (collected from patients in Phase III clinical test of Compound II-6 and stored in an ultra-low-temperature freezer), and a medium for cell control were diluted 101 to 107 folds by a 10-fold serial dilution method.

(3) After cells present in a sheet form were confirmed under an inverted microscope, the medium was removed, and a new medium was added at 100 μL/well.

(4) The medium was removed.

(5) Each of the samples (100 to 107) prepared at (2) above was inoculated at 100 μL/well, using 4 wells per sample.

(6) Centrifugal adsorption was performed at room temperature at 1000 rpm for 30 minutes.

(7) After centrifugation, the medium was removed, and cells were washed once with a new medium.

(8) A new medium was added at 100 μL/well.

(9) Incubation was performed in a 5% $CO_2$ incubator at 33±1° C. for 3 days.

(10) After incubation, the CytoPathic Effect (CPE) was evaluated under an inverted microscope.

Method for Determining to have a Positive Virus Titer

When the detection limit was exceeded as measured by the above virus titer measurement method, it was determined to be positive.

Analysis of Primary Endpoint

As for the time to alleviation of influenza symptoms, which is the primary endpoint, the primary analysis and the secondary analysis are described. The primary analysis was performed on the ITTI group.

(1) Primary Analysis

For patients at 12 to 64 years old, the placebo group and the investigational drug administered group were compared by stratified generalized Wilcoxon test using the total score of 7 influenza symptoms before administration (11 points or less, 12 points or more) and regions (Japan/Asia, other regions) as stratification factors.

Also, a Kaplan-Meier survival curve was drawn for each group to calculate the median time to alleviation of influenza symptoms and the 95% confidence interval thereof as well as the difference between the groups in the time to alleviation of influenza symptoms and the 95% confidence interval thereof.

(2) Secondary Analysis

For patients at 20 to 64 years old, the time to alleviation of influenza symptoms was compared between the Compound II-6 group and the Oseltamivir group by the same method as the primary analysis.

Analysis of Secondary Endpoint

The following secondary efficacy endpoints were compared between the Compound II-6 group and the placebo group and between the Compound II-6 group and the Oseltamivir group (the age group of 20 to 64 years old).

(1) Proportion of Patients Having a Positive Influenza Virus Titer at Various Time Points Only the patients having a virus titer equal to or greater than the determination limit before the beginning of administration in Visit 1 were included in the analysis. In each Visit, a Mantel-Haenszel test using the total score of 7 influenza symptoms before administration and the regions as stratification factors was applied, and the proportion of patients having a positive virus titer was compared between two groups.

(2) Amount of Change in Virus Titer from Baseline at Various Time Points

Only the patients having a virus titer before the beginning of administration in Visit 1 were included in the analysis. In each Visit, a van Elteren test using the total score of 7 influenza symptoms before administration and the regions as stratification factors was applied, and the amount of change in influenza virus titer from the baseline was compared between two groups.

(3) Time to Termination of Viral Shedding Based on Virus Titer

Only the patients having a virus titer equal to or greater than the determination limit before the beginning of administration in Visit 1 were included in the analysis. A stratified generalized Wilcoxon test using the total score of 7 influenza symptoms before administration and the regions as stratification factors was applied.

(4) Incidence of Side Effects

The number of side-effect episodes and the number of patients with side effect were counted for each administration group.

(1) Results of Primary Endpoint (Time to Alleviation of Influenza Symptoms)

Out of 1436 randomly selected patients, 1366 patients (578 patients in the 40 mg or 80 mg Compound II-6 administered group, 498 patients in the Oseltamivir administered group, and 290 patients in the placebo group) completed the test. As for the primary endpoint, the ITTI cases (cases where GCP was followed, the investigational drug was administered, and influenza virus infection was confirmed) consisted of 1064 patients.

The per protocol set cases consisted of 990 patients (427 patients in the 40 mg or 80 mg Compound II-6 administered group, 351 patients in the Oseltamivir administered group, and 212 patients in the placebo group).

Analysis results are shown in the following table.

TABLE 23

| | 12 Years old or older and younger than 65 years old | | 20 Years old or older and younger than 65 years old | |
| --- | --- | --- | --- | --- |
| | Compound II-6 administered group | Placebo administered group | Compound II-6 administered group | Oseltamivir administered group |
| Number of patients | 455 | 230 | 375 | 377 |
| Median (hour) | 53.7 | 80.2 | 53.5 | 53.8 |
| 95% Confidence interval (hour) | 49.5, 58.5 | 72.6, 87.1 | 48.0, 58.5 | 50.2, 56.4 |
| Difference between groups [a] (hour) | −26.5 | — | −0.3 | — |
| 95% Confidence interval of difference between groups (hour) [b] | −35.8, −17.8 | — | −6.6, 6.6 | — |
| Stratified generalized Wilcoxon test[c] p Value [a] | <.0001 | — | 0.7560 | — |

[a] vs Placebo or vs Oseltamivir

[b] Bootstrap estimation

[c]Used the regions and the total score of 7 influenza symptoms before administration as stratification factors, and censored at final evaluation for patients whose symptoms were no alleviated.

In the ITTI group, the time to alleviation of influenza symptoms (median) (95% CI) was 53.7 hours (95% CI: 49.5, 58.5) in the Compound II-6 group while 80.2 hours (95% CI: 72.6, 87.1) in the placebo group, and the difference between the Compound II-6 group and the placebo group was −26.5 hours. The time to alleviation of influenza symptoms of the Compound II-6 group was significantly shorter than that of the placebo group in the primary analysis using a stratified generalized Wilcoxon test (p<0.0001).

In the subgroup of patients at 20 years old or older and younger than 65 years old, the time to alleviation of influenza symptoms was 53.5 hours (95% CI: 48.0, 58.5) in the Compound II-6 group while 53.8 hours (95% CI: 50.2, 56.4) in the Oseltamivir group, and the difference between the Compound II-6 group and the Oseltamivir group was −0.3 hours. There was no significant difference between the times to alleviation of influenza symptoms of the Compound II-6 group and the Oseltamivir group in the stratified generalized Wilcoxon test.

Analysis of Secondary Endpoint (1) Proportion of Patients Having a Positive Influenza Virus Titer at Various Points Analysis results are shown in the following table.

TABLE 24

| Observation time point | | 12 Years old or older and younger than 65 years old | | 20 Years old or older and younger than 65 years old | |
|---|---|---|---|---|---|
| | | Compound II-6 administered group N = 427 | Placebo administered group N = 210 | Compound II-6 administered group N = 352 | Oseltamivir administered group N = 359 |
| Day 2 | Proportion | 47.8% (197/412) | 96.0% (193/201) | 47.6% (161/338) | 91.0% (315/346) |
| | 95% Confidence interval | 42.9, 52.8 | 92.3, 98.3 | 42.2, 53.1 | 87.5, 93.8 |
| | p Value $^a$ | <.0001 | — | <.0001 | — |
| Day 3 | Proportion | 21.5% (87/404) | 70.2% (134/191) | 19.8% (66/333) | 57.3% (197/344) |
| | 95% Confidence interval | 17.6, 25.9 | 63.1, 76.5 | 15.7, 24.5 | 51.9, 62.6 |
| | p Value $^a$ | <.0001 | — | <.0001 | — |
| Day 4 | Proportion | 16.7% (19/114) | 56.1% (32/57) | 16.1% (14/87) | 27.6% (29/105) |
| | 95% Confidence interval | 10.3, 24.8 | 42.4, 69.3 | 9.1, 25.5 | 19.3, 37.2 |
| | p Value $^a$ | <.0001 | — | 0.0852 | — |
| Day 5 | Proportion | 13.6% (55/403) | 29.7% (57/192) | 13.0% (43/331) | 20.9% (70/335) |
| | 95% Confidence interval | 10.4, 17.4 | 23.3, 36.7 | 9.6, 17.1 | 16.7, 25.6 |
| | p Value $^a$ | <.0001 | — | 0.0066 | — |
| Day 6 | Proportion | 8.2% (8/97) | 12.5% (6/48) | 5.6% (4/71) | 9.0% (7/78) |
| | 95% Confidence interval | 3.6, 15.6 | 4.7, 25.2 | 1.6, 13.8 | 3.7, 17.6 |
| | p Value $^a$ | 0.4767 | — | 0.6187 | — |
| Day 9 | Proportion | 2.9% (12/407) | 4.6% (9/197) | 3.0% (10/335) | 3.2% (11/339) |
| | 95% Confidence interval | 1.5, 5.1 | 2.1, 8.5 | 1.4, 5.4 | 1.6, 5.7 |
| | p Value $^a$ | 0.3379 | — | 0.8618 | — |

Day 2 indicates 24 hours later, as counted from the first day of administration, Day 3 indicates 48 hours later, Day 4 indicates 72 hours later, Day 5 indicates 96 hours later, Day 6 indicates 120 hours later, and Day 9 indicates 192 hours later.

a vs Placebo or vs Oseltamivir. Mantel-Haenszel test. Used the regions and the total score of 7 influenza symptoms before administration as stratification factors, and intended for a group having a positive virus titer before administration.

The proportion of patients having a positive virus titer was significantly lower in the Compound II-6 group than in the placebo group on Day 2 (Mantel-Haenszel test: p<0.0001), and likewise, significantly lower in the Compound II-6 group than in the placebo group on Day 3 (p<0.0001). In the subgroup of patients at 20 years old or older and younger than 65 years old, the proportion of patients having a positive virus titer was significantly lower in the Compound II-6 group than in the Oseltamivir group on Day 2 and Day 3 (p<0.0001).

(2) Amount of Change in Virus Titer from Baseline at Various Points

Analysis results are shown in the following table.

TABLE 25

| Observation time point | | 12 Years old or older and younger than 65 years old | | 20 Years old or older and younger than 65 years old | |
|---|---|---|---|---|---|
| | | Compound II-6 administered group N = 427 | Placebo administered group N = 210 | Compound II-6 administered group N = 352 | Oseltamivir administered group N = 359 |
| Day 2 | Number of patients | 412 | 201 | 338 | 346 |
| | Mean | −4.44 | −1.19 | −4.39 | −2.51 |
| | Standard deviation | 2.03 | 2.43 | 2.07 | 2.03 |
| | p Value [a] | <.0001 | — | <.0001 | — |
| Day 3 | Number of patients | 404 | 191 | 333 | 344 |
| | Mean | −4.82 | −2.91 | −4.78 | −4.20 |
| | Standard deviation | 1.99 | 2.85 | 2.03 | 2.02 |
| | p Value [a] | <.0001 | — | <.0001 | — |
| Day 4 | Number of patients | 114 | 57 | 87 | 105 |
| | Mean | −4.50 | −3.31 | −4.46 | −4.63 |
| | Standard deviation | 2.02 | 2.34 | 2.03 | 1.89 |
| | p Value [a] | 0.0008 | — | 0.8010 | — |
| Day 5 | Number of patients | 403 | 192 | 331 | 335 |
| | Mean | −4.95 | −4.47 | −4.95 | −4.98 |
| | Standard deviation | 1.93 | 2.21 | 1.94 | 1.82 |
| | p Value [a] | 0.0132 | — | 0.9425 | — |
| Day 6 | Number of patients | 97 | 48 | 71 | 78 |
| | Mean | −4.58 | −4.68 | −4.56 | −4.85 |
| | Standard deviation | 1.99 | 2.12 | 1.99 | 1.95 |
| | p Value [a] | 0.9307 | — | 0.2256 | — |
| Day 9 | Number of patients | 407 | 197 | 335 | 339 |
| | Mean | −5.06 | −4.87 | −5.03 | −5.22 |
| | Standard deviation | 1.87 | 1.85 | 1.89 | 1.70 |
| | p Value [a] | 0.1684 | — | 0.3267 | — |

Unit: $\log_{10}$ [TCID$_{50}$/mL].
Day 2 indicates 24 hours later, as counted from the first day of administration, Day 3 indicates 48 hours later, Day 4 indicates 72 hours later, Day 5 indicates 96 hours later, Day 6 indicates 120 hours later, and Day 9 indicates 192 hours later.
[a] vs Placebo or vs Oseltamivir. van Elteren test. Used the regions and the total score of 7 influenza symptoms before administration as stratification factors. Intended for a group having a positive virus titer before administration.

The virus titer decreased significantly in the Compound II-6 group as compared to the placebo group on Day 2, and likewise, decreased significantly as compared to the placebo group on Day 3 (van Elteren test: p<0.0001). In the subgroup of patients at 20 years old or older and younger than 65 years old, the virus titer decreased significantly in the Compound II-6 group as compared to the Oseltamivir group on Day 2 and Day 3 (p<0.0001).

(3) Time to Termination of Viral Shedding Based on Virus Titer

Analysis results are shown in the following table.

Censored at final evaluation for patients whose virus titer was not eliminated. Intended for analyzing patients who had a positive virus titer on Day 1 and whose data concerning the time to termination of viral shedding was not missing.

The time (median) to termination of viral shedding based on virus titer was 24.0 hours in the Compound II-6 group while 96.0 hours in the placebo group, and was significantly shorter in the Compound II-6 group than in the placebo group (stratified generalized Wilcoxon test: p<0.0001). The time to termination of viral shedding in the subgroup of patients at 20 years old or older and younger than 65 years

TABLE 26

| | 12 Years old or older and younger than 65 years old | | 20 Years old or older and younger than 65 years old | |
|---|---|---|---|---|
| | Compound II-6 administered group | Placebo administered group | Compound II-6 administered group | Oseltamivir administered group |
| Number of patients | 423 | 207 | 348 | 355 |
| 95% Confidence interval (hour) | 24.0, 48.0 | — | 24.0, 48.0 | 72.0, 96.0 |
| Difference between groups (hour) [a] | −72.0 | — | −48.0 | — |
| Stratified generalized Wilcoxon test [b] p Value | <.0001 | — | <.0001 | — |

[a] vs Placebo or vs Oseltamivir.
[b] Used the regions and the total score of 7 influenza symptoms before administration as stratification factors.

old was 24.0 hours in the Compound II-6 group and 72.0 hours in the Oseltamivir group, and was significantly shorter in the Compound II-6 group than in the Oseltamivir group (p<0.0001).

(4) Incidence of Adverse Events

Severe adverse events the causal relationship of which cannot be denied are not reported. Adverse events the causal relationship of which cannot be denied occurred in 27 patients out of 610 patients (4.4%, 37 episodes) in the Compound II-6 group, 12 patients out of 309 patients (3.9%, 19 episodes) in the placebo group, and 43 patients out of 513 patients (8.4%, 53 episodes) in the Oseltamivir group. There was no statistically significant difference between the incidences in the Compound II-6 group and the placebo group (Fisher's exact test, two-sided P value: 0.8627). However, the incidence in the Compound II-6 group was significantly lower than that in the Oseltamivir group (Fisher's exact test, two-sided P value: 0.0088).

Clinical Test (Ph3: Child)

The efficacy and safety of a single oral administration of an investigational drug (active ingredient (Compound II-6): 5 mg, 10 mg, 20 mg, 40 mg) to patients infected by influenza virus were evaluated. As for the primary endpoint, guardians or subjects by themselves made evaluations and measurements concerning the time to alleviation of influenza symptoms (the time from the beginning of administration of the investigational drug until influenza symptoms ("cough", "runny nose/nasal congestion", and "fever") were alleviated) to evaluate the efficacy of the investigational drug.

"Cough" and "runny nose/nasal congestion" were evaluated on a 4-point scale [0: none, 1: mild, 2: moderate, 3: severe].

Patients who satisfied all of the following criteria were selected as subjects.

(a) Male or female patients at 6 months old or older and younger than 12 years old
(b) Patients satisfying all of the following criteria and diagnosed with influenza virus infectious disease
  Positive in influenza rapid diagnosis [Rapid antigen test (RAT)] based on a nasal or throat swab
  Body temperature (axillary temperature) of 38.0° C. or higher
  Having one or more moderate or severer symptoms among the respiratory symptoms due to influenza virus infectious disease for patients at 7 years old or older
(c) Patients within 48 hours from onset (at registration). The onset is defined as when the body temperature exceeding 37.5° C. is confirmed for the first time.
(d) Patients having a body weight of 5 kg or more.

Method for Administering Investigational Drug
(i) Test Drug
5 mg Tablet of Compound II-6: Half of 10 mg tablet of Compound II-6
10 mg Tablet of Compound II-6
20 mg Tablet of Compound II-6

Dosage and Administration Method

Patients received a single oral administration on Day 1 in a dose calculated based on the body weight (see the table below).

TABLE 27

| Body weight of patient at the time of screening | Dose of Compound II-6 | Compound II-6 tablet |
|---|---|---|
| 5 kg or more and less than 10 kg | 5 mg | Half of 10 mg tablet |
| 10 kg or more and less than 20 kg | 10 mg | One 10 mg tablet |
| 20 kg or more and less than 40 kg | 20 mg | One 20 mg tablet or two 10 mg tablets |
| 40 kg or more | 40 mg | Two 20 mg tablets |

Main Efficacy Endpoint

The main efficacy endpoint is the time to alleviation of influenza symptoms (the time to alleviation of influenza symptoms).

It is the time from the beginning of administration until alleviation of influenza symptoms. Alleviation of an influenza symptom refers to the time when a and b below are satisfied from the beginning of administration, and this clinical condition continues at least 21.5 hours (24 hours—10%).

a. "Cough" and "runny nose/nasal congestion" are both "0: none" or "1: mild" in the patient diary b. Body temperature (axillary temperature) is lower than 37.5° C.

Analysis of Primary Endpoint

As for the time to alleviation of influenza symptoms, which is the primary endpoint, the primary analysis is described. The primary analysis was performed on the ITTI group.

(1) Primary Analysis

A Kaplan-Meier curve of the time to alleviation of influenza symptoms ("cough", "runny nose/nasal congestion", and "fever") (the time to alleviation of influenza symptoms) was drawn to calculate the median time to complete alleviation of influenza symptoms and the 95% confidence interval thereof. Patients whose influenza symptoms were not completely alleviated during the observation period were treated as censored cases.

(1) Results of Primary Endpoint (Time to Alleviation of Influenza Symptoms)

As for the primary endpoint, 103 patients were involved. The time (median) to alleviation of influenza symptoms in the ITTI group was 44.6 hours (95% CI: 38.9, 62.5)

INDUSTRIAL APPLICABILITY

A novel finding that a color difference of a preparation containing a compound represented by formula (I) is increased by irradiating the preparation with light was found. Therefore, the color difference of the preparation can be reduced by coating the surface of the preparation with a light stabilizing substance and a polymer. In this manner, the preparation containing the compound represented by formula (I) can be stably stored under irradiation with light.

The invention claimed is:

1. A solid preparation comprising:
a compound represented by the formula (I):

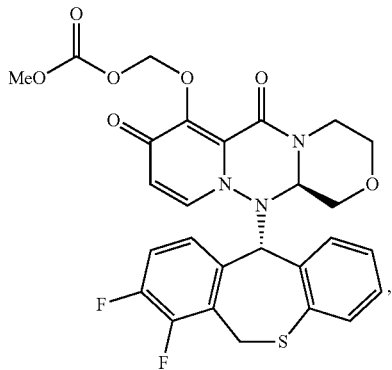

(I)

or a pharmaceutically acceptable salt thereof,
croscarmellose sodium, and
a coating layer comprising at least one light-stabilizing substance and at least one polymer selected from the group consisting of hypromellose, polyvinyl alcohol and hydroxypropyl cellulose,
wherein the solid preparation is in the form of a tablet, and the tablet is coated by the coating layer.

2. The solid preparation according to claim 1, wherein the light-stabilizing substance in the coating layer is at least one selected from the group consisting of edible tar dye, edible lake tar dye, edible natural dye, ferric oxide, titanium oxide and talc.

3. The solid preparation according to claim 1, wherein the light-stabilizing substance in the coating layer is at least one selected from the group consisting of Food Red No. 2, Food Red No. 3, Food Red No. 102, Food Red No. 104, Food Red No. 105, Food Red No. 106, Food Yellow No. 4, Food Yellow No. 5, Food Green No. 3, Food Blue No. 1, Food Blue No. 2, Food Red No. 3 aluminum lake, Food Yellow No. 4 aluminum lake, Food Yellow No. 5 aluminum lake, Food Blue No. 1 aluminum lake, Food Blue No. 2 aluminum lake, carmine, sodium copper chiorophyllin, copper chlorophyll, red oxide, red ferric oxide, yellow ferric oxide, black iron oxide, yellow oxide of iron, titanium oxide and talc.

4. The solid preparation according to claim 3, wherein the light-stabilizing substance in the coating layer is at least one selected from the group consisting of red ferric oxide, yellow ferric oxide, black iron oxide, yellow oxide of iron, titanium oxide and talc.

5. The solid preparation according to claim 4, wherein the light-stabilizing substance in the coating layer is at least one selected from the group consisting of titanium oxide and talc.

6. The solid preparation according to claim 1, wherein the polymer in the coating layer is at least one selected from the group consisting of hypromellose and hydroxypropyl cellulose.

7. The solid preparation according to claim 6, wherein the polymer is hypromellose.

8. The solid preparation according to claim 1, wherein the light stabilizing substance is at least one selected from the group consisting of titanium oxide and talc, and the polymer is hypromellose in the coating layer.

9. The solid preparation according to claim 1, wherein the color difference ΔE is not more than 13 at optical illumination of 1.2 million lux.

10. The solid preparation according to claim 1, which is packaged in an aluminum blister package.

11. The solid preparation according to claim 1, wherein a release rate of the compound represented by formula (I) is not less than 80% after 45 minutes of initiation of a dissolution test.

12. The solid preparation according to claim 1, which comprises an amount of the compound represented by formula (I) of 10 mg, 20 mg, 40 mg or 80 mg.

13. The solid preparation according to claim 1, comprising:
the compound represented by formula (I) in an amount of 40 mg or 80 mg,
the croscarmellose sodium in an amount of 1 to 10% by weight based on the total amount of the solid preparation, and
a coating layer comprising titanium oxide, talc and the at least one polymer,
wherein the solid preparation further comprises:
a lubricant in an amount of 0.1 to 5 % by weight based on the total amount of the solid preparation, and
a binder in an amount of 0.5 to 10% by weight based on the total amount of the solid preparation.

14. The solid preparation according to claim 1, comprising:
the compound represented by formula (I) in an amount of 40 mg or 80 mg,
the croscarmellose sodium in an amount of 1 to 10% by weight based on the total amount of the solid preparation, and
a coating layer comprising titanium oxide, talc and hypromellose,
wherein the solid preparation further comprises:
sodium stearyl fumarate in an amount of 0.1 to 5% by weight based on the total amount of the solid preparation, and
polyvinyl pyrrolidone in an amount of 0.5 to 10% by weight based on the total amount of the solid preparation.

* * * * *